US005539104A

United States Patent [19]

Callahan et al.

[11] Patent Number: 5,539,104
[45] Date of Patent: Jul. 23, 1996

[54] 1,4 DIAZOCINES AS FIBRINOGEN ANTAGONISTS

[75] Inventors: James F. Callahan, Philadelphia; William F. Huffman, Malvern, both of Pa.

[73] Assignee: SmithKline Beecham Corp., Philadelphia, Pa.

[21] Appl. No.: 232,169

[22] PCT Filed: Oct. 30, 1992

[86] PCT No.: PCT/US92/09467

§ 371 Date: Apr. 29, 1994

§ 102(e) Date: Apr. 29, 1994

Related U.S. Application Data

[63] Continuation-in-part of Ser. No. 785,672, Oct. 31, 1991, abandoned.

[51] Int. Cl.$^6$ .............................. C07K 5/02; C07K 5/06; C07K 5/08; C07K 15/00; C07D 245/02; F61K 37/02
[52] U.S. Cl. .............................. 540/460; 540/451
[58] Field of Search .................. 540/460, 451; 514/183

[56] References Cited

U.S. PATENT DOCUMENTS

| 4,167,512 | 9/1979 | Lai .................................. 540/460 X |
| 4,339,381 | 7/1982 | Richter et al. .................. 540/460 X |
| 4,692,510 | 9/1987 | Konishi et al. .................. 40/460 X |
| 4,746,737 | 5/1988 | Fujii et al. ..................... 540/460 X |

FOREIGN PATENT DOCUMENTS

| 0001284 | 4/1979 | European Pat. Off. ........... 540/460 |
| 0010243 | 4/1980 | European Pat. Off. ........... 540/460 |
| 63-205651 | 8/1988 | Japan ............................. 540/460 |

OTHER PUBLICATIONS

Huffman et al, Peptides Chemistry & Biol., 10th Symposium, pp. 105–108 (1988).

*Primary Examiner*—Floyd D. Higel
*Attorney, Agent, or Firm*—Charles M. Kinzig; Stephen Venetianer; Edward T. Lentz

[57] ABSTRACT

This invention relates to a method of inhibiting platelet aggregation using 1,4-diazocine compounds which are mimics of the peptide sequence Arg—Gly—Asp.

10 Claims, No Drawings

1,4 DIAZOCINES AS FIBRINOGEN ANTAGONISTS

This is a continuation-in-part of U.S. patent application Ser. No. 07/785,672, filed Oct. 31, 1991, now abandoned.

FIELD OF THE INVENTION

This invention relates to novel compounds which inhibit platelet aggregation, pharmaceutical compositions containing the compounds and methods of using the compounds for inhibiting platelet aggregation. A method of using the compounds of this invention in combination with fibrinolytic agents is also disclosed.

BACKGROUND OF THE INVENTION

A thrombus is the result of processes which initiate the coagulation cascade. It is composed of an aggregation of platelets enmeshed in a polymeric network of fibrin. This process is normally initiated as a consequence of tissue injury and has the effect of slowing or preventing blood flow in a vessel. Etiological factors which are not directly related to tissue injury, such as atherosclerotic plaque, inflammation of the blood vessels (phlebitis) and septicemia, may also initiate thrombus formation. In some instances, the inappropriate formation of a thrombus, and subsequent decrease in blood flow, may have pathological consequences, such as stroke, pulmonary embolism and heart disease.

Platelets play a major role in thrombus formation. Current antithrombotic therapy employs agents that modify the platelet/endothelial cell arachidonate-prostaglandin system, such as prostacyclin analogues, cyclooxygenase inhibitors, thromboxane synthesis inhibitors and thromboxane receptor antagonists; and anti-coagulants, such as heparin. These agents inhibit one or both of two discernible phases of platelet aggregation. The primary phase, which is a response to chemical stimuli, such as ADP (adenosine diphosphate), collagen, epinephrine or thrombin, causes initial activation of the platelets. This is followed by a secondary phase, which is initiated by the platelets themselves, and is characterized by thromboxane $A_2$ ($TxA_2$) synthesis and the release of additional ADP from platelet storage granules, which further activates platelets.

Prostacyclin, also called prostaglandin $I_2$ (PGI2), and stable $PGI_2$ analogues inhibit both the primary and secondary phases of platelet aggregation. However, use of such analogues has been associated with undesirable changes in blood pressure. See Aiken, et al., *Prostaglandins*, 19, 629–43 (1980).

Cyclooxygenase inhibitors and thromboxane synthetase inhibitors act to block the production of $TxA_2$. $TxA_2$ antagonists block the effects of $TxA_2$ by binding the $TxA_2$ receptor. These therapies act only upon the secondary stage of platelet activation. Use of cyclooxygenase inhibitors has been associated with ulcerogenesis and an adverse effect upon prostacyclin synthesis.

Heparin prevents the activation of fibrinogen by thrombin and thereby prevents the activation of the GPIIb-IIIa receptor by thrombin. This inhibits only the primary phase of platelet aggregation and has little effect upon activation of platelets by other means, such as collagen, ADP and epinephrine.

Cyclooxygenase inhibitors, prostaglandin analogues and heparin all inhibit platelet aggregation indirectly by inhibiting the primary or secondary phase of platelet/fibrinogen activation. There is therefore a need for selective therapeutic products which block platelet aggregation directly, whether it arises from the primary or secondary phase of platelet activation.

Platelet aggregation is believed to be mediated primarily through the GPIIb-IIIa platelet receptor complex, which is also called the fibrinogen receptor. Von Willebrand factor, a plasma protein, and fibrinogen are able to bind and crosslink GPIIb-IIIa receptors on adjacent platelets and thereby effect aggregation of platelets. Preventing the binding and crosslinking of GPIIb-IIIa receptors is believed to be method of inhibiting platelet aggregation.

GPIIb-IIIa is a member of a larger class of receptor proteins, called integrins, which mediate adhesive functions. Fibronectin, vitronectin and thrombospondin are proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls, and aid in arresting blood flow from a damaged vessel. It is desirable to be able to interrupt the interaction of platelets with fibrinogen, selectively, without having a major effect upon their interactions with the structural proteins.

Peptide fragments of human plasma fibronectin and synthetic peptides containing an RGD (single letter amino acid code for Arg—Gly—Asp) sequence which promote cell attachment and enhance phagocytosis are disclosed in U.S. Pat. Nos. 517,686, 4,589,881, 4,661,111 and U.S. Pat. No. 4,614,517. Linear and cyclic peptides containing an RGD sequence have also been reported in WO 89/05150 (PCT US88/04403). Peptides which contain an RGD sequence have been reported to inhibit platelet aggregation. Nievelstein et al. *Thromb. and Hemostasis*, 58, 2133 (1987) have reported that -RGDS- peptides inhibit thrombin induced aggregation and adhesion of platelets to fibronectin, and may interact through the GPIIb-IIIa complex. U.S. Pat. No. 4,683,291 discloses peptides containing Arg and Lys and an -RGD- sequence which inhibit binding of fibrinogen to platelets and inhibit platelet aggregation. A disadvantage of these peptides is their poor stability in plasma and their low potency. EP 0 275 748 discloses linear tetra- to hexapeptides and cyclic hexa- to octapeptides which bind to the GPIIb-IIIa receptor and inhibit platelet aggregation. Other linear and cyclic peptides, the disclosure of which are incorporated herein by reference, are reported in EP-A 0 341 915. Inhibitors of the fibrinogen receptor which are not based upon natural amino acid sequences are disclosed in EP-A 0 372,468 and EP-A 0 381 033. However, there remains a need for fibrinogen receptor antagonists which are potent and show a high selectivity for the fibrinogen receptor relative to other matrix proteins.

The instant invention provides novel 1,4-diazocine compounds which have increased selectivity toward the fibrinogen receptor.

SUMMARY OF THE INVENTION

One object of this invention is to provide a method for inhibiting platelet aggregation. A feature of this invention is a method for inhibiting the GPIIb-IIIa receptor selectively, relative to other integrins.

Another feature of this invention is a compound of the formula (I):

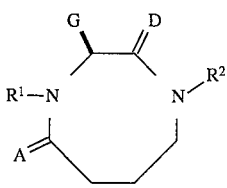

(I)

wherein A, D, G, $R^1$ and $R^2$ are described hereinafter.

In another aspect, this invention is a pharmaceutical composition comprising a compound of formula (I) and a pharmaceutically acceptable carrier. The method of inhibiting platelet aggregation comprises administering an effective amount of a compound of formula (I).

Another object of this invention is to provide a method for effecting thrombolysis and inhibiting reocclusion of an artery or vein in a mammal. The method comprises internally administering to a mammal in need thereof, an effective amount of a fibrinolytic agent and a compound of formula (I).

A feature of this invention is a pharmaceutical composition comprising a fibrinolytic agent and a compound of formula (I). Yet another feature of this invention is a kit which comprises, in separate containers, a fibrinolytic agent and a compound of formula (I).

DETAILED DESCRIPTION OF THE INVENTION

The compounds of this invention inhibit platelet aggregation and are believed to interact with the GPIIb-IIIa receptor. Receptor antagonists, in general, are believed to interact favorably with receptors by being capable of adopting a conformation which binds in a complementary manner to the receptor. Thus, in order to bind to the receptor, the antagonist must possess the proper functional groups, and the ability to present them in a spatially appropriate manner. Even simple linear molecules, such as Arg—Gly—Asp, may adopt an innumerable variety of conformations. However, only a limited number of these may approximate the binding site of a receptor. Thus, one method of constructing receptor antagonists provides for constraining the spatial arrangement of the atoms of the putative antagonist by incorporating them into a ring structure. This is complicated by the fact that one can rarely predict what conformation is necessary to effect binding, and because a change in one portion of a molecule can often have unexpected consequences for other parts of the same molecule. Accordingly, the present invention provides molecules which are believed to mimic the conformation of the Arg—Gly—Asp sequence of fibrinogen as it is presented to the GPIIb-IIIa receptor. The compounds of this invention are presumed to constrain the side chain of a putative arginine residue into a favorable conformation, relative to other portions of the molecule, for specific interaction with the fibrinogen receptor.

This invention comprises compounds of the formula (I):

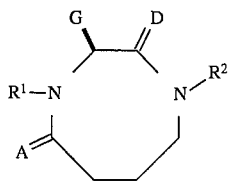

(I)

wherein

A, D and E are independently O or (H,H);

G is $(CHR^7)_t$—Y, $(CHR^7)_p$—Het—$(CH_2)_p$—Y, $(CHR^7)_p$—C3-7cycloalkyl—$(CH_2)_p$—Y or

;

X is absent, N=CR', C(O) or O;

Y is R'R"N—, R'R"NR'N—, R'R"NR'NCO—, $R'_2$NR'NC(=NR')—, R'ONR'C(=NR')—,

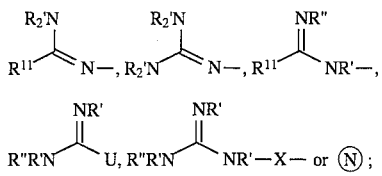

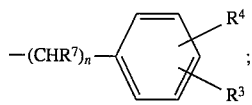—X— or 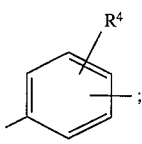;

R' is H, $C_{1-6}$alkyl, $C_{3-7}$cycloalkyl—$C_{0-4}$alkyl or Ar—$C_{0-4}$alkyl;

R" is R' or —C(O)R';

$R^1$ is L-M, wherein L is H, $R^6$, $R^6$—J—CO or $R^6$—J—S$(O)_m$, J is O, NH, S or a covalent bond, and M is —NH($CHR^9$)CO— or a covalent bond;

$R^2$ is $(CH_2)_m$(C=E)—Q—CH($R^3$) ($R^4$) or

—$(CHR^7)_n$—⟨phenyl with $R^4$, $R^3$⟩;

Q is a covalent bond, $NR^7$, O, S, $CH_2$ or

⟨phenyl with $R^4$⟩;

$R^3$ is H, $(CHR^7)_u$—$R^{10}$, or O$(CHR^7)_v$—$R^{10}$ or $(CHR^7)_n$CH(NH—L)—$R^{10}$;

$R^4$ is H, $(CHR^7)_u$CO—V, O$(CHR^7)_v$CO—V, $(CHR^7)_u$—W or O$(CHR^7)_v$—W;

U is absent, S or O;

V is W, NHCH $(R^5)$CO—W or OCH($R^5$)CO—W;

W is $NHR^6$, $OR^6$ or $R^6$;

$R^5$ and $R^9$ are H $C_{1-6}$alkyl, $C_{3-6}$cycloalkyl, $(CH_2)_n$—Ar, $(CH_2)_n$—Het or $(CH_2)_q$Z, where Z is $C_{3-6}$cycloalkyl OH, $NH_2$, SH, S—$C_{1-4}$alkyl, $CO_2R^8$, $CONH_2$ or NHC(=NH)$NH_2$;

$R^6$ is H, $(CHR^7)_r$—H, $(CHR^7)_r$—$C_{3-6}$cycloalkyl, $(CHR^7)_r$—Ar, $(CHR^7)_r$—Het;

$R^7$ is H or $C_{1-4}$alkyl;

$R^8$ is H or $C_{1-4}$alkyl;

$R^{10}$ is $CO_2H$, $SO_3H$, Tet;

$R^{11}$ is R', —$CF_3$, —SR', or —OR';

m is 1 or 2;

n is 0 to 2;

p is 0 to 2;

q is 1 to 4;

r is 0 to 4;

t is 2 to 5;

u is 0 to 4;

v is 1 to 3;

or a pharmaceutically acceptable salt thereof.

Suitably D and E are O.

Suitably G is $(CH_2)_3NHC(=NH)NH_2$.

Suitably $R^1$ is H, $C_{1-2}$alkyl, acetyl or benzoyl. Preferably $R^1$ is methyl or acetyl.

Suitably $R^2$ is $CH_2CONHCH(R^3)CO$—V.

Suitably $R^3$ is $CH_2CO_2H$.

Suitably V is OH, $NH_2$, NHPh, or a natural amino acid. Preferably V is NHPh.

Preferably A is (H,H), D is O, and $R^2$ is $CH_2CONHCH(CH_2CO_2H)CO$—NHPh.

Specific compounds of this invention are:

N-[2-oxo-3-(S)-[3-guanidinopropyl]-octahydro-1,4-diazocin-1-yl]-acetyl-aspartyl-1-phenylamide;

N-[2-oxo-3-(S)-[3-guanidinopropyl]-4-acetyl-octahydro-1,4-diazocin-1-yl]-acetyl-aspartyl-1-phenylamide;

N-[2,5-dioxo-3-(S)-[3-guanidinopropyl]-4-methyl-octahydro-1,4-diazocin-1-yl]-acetyl-aspartyl-1-phenylamide;

N-[2,5-dioxo-3-(S)-[3-guanidinopropyl]-4-methyl-octahydro-1,4-diazocin-1-yl]-acetyl-β-alanine;

N-[2,5-dioxo-3-(S)-[3-guanidinopropyl]-4-methyl-octahydro-1,4-diazocin-1-yl]-aspartyl-valinyl acid;

N-[2,5-dioxo-3-(S)-[3-guanidinopropyl]-octahydro-1,4-diazocin-1-yl]-acetyl-aspartyl-1-phenylamide.

The meaning of each variable substituent of formula (I) at any occurrence in the formula is independent of its meaning at every other occurrence. The compounds described herein may have one or more chiral centers. It will be understood that that this invention includes each unique nonracemic compound which may be synthesized and resolved by conventional techniques, as well as racemic or diastereomeric mixtures thereof.

In general, the amino acid abbreviations follow the IUPAC-IUB Joint Commission on Biochemical Nomenclature as described in *Eur. J. Biochem.*, 158, 9 (1984). A natural amino acid is a naturally occurring α-amino acid, such as Ala, Arg, Asp, Asn, Cys, Glu, Gln, Gly, His, Ile, Leu, Lys, Met, Orn, Phe, Pro, ser, Thr, Trp, Tyr, or Val. A modified amino acid is a non-naturally occurring amino acid which is available by synthetic techniques which are routine in the art, such as Nle, Pen, APmp, Nal, Dtc, and Tpr. The residues M and V may be natural or modified amino acids. V is preferably Val, Phe, Trp, Nal, Cys, Met, APmp or Pen. M is preferably Arg, Abu, Ala, Gly, His, Lys, Dtc, Tpr or Pro. The moiety L is a substituent upon the amino group of the M residue.

Het, or heterocycle, indicates a five or six membered monocyclic ring, or a nine or ten-membered bicyclic ring, containing one to three heteroatoms chosen from the group of nitrogen, oxygen and sulfur, which are stable and available by conventional chemical synthesis. Representative heterocycles are pyridyl, pyrrolyl, pyrrolinyl, pyrrolidinyl, indolyl, imidazolyl, benzimidazolyl, benzofuryl, benzothiazolyl, quinolinyl, furyl, thiazolyl, thiazolinyl and thienyl. The heterocycle may be optionally substituted by one or two $C_{1-4}$alkyl, $C_{1-4}$alkoxy, $CO_2R'$, $CON(R')_2$, $NR'_2$, OR' or SR', wherein R' is H, $C_{1-4}$alkyl, phenyl or benzyl.

Ar is phenyl or naphthyl optionally substituted by one or two $C_{1-4}$alkyl, $C_{1-4}$alkoxy, $C_{1-5}$alkylthio, $CO_2R'$ $CON(R')_2$, $NR'_2$, hydroxy, halogen, trifluoromethyl or nitro groups.

$C_{1-4}$alkyl as applied herein is meant to include methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g. that a covalent bond is present).

$C_{3-6}$cycloalkyl refers to an optionally substituted carbocyclic system of three to six carbon atoms, which may contain up to two unsaturated carbon-carbon bonds. Typical of $C_{3-6}$cycloalkyl are cyclopropyl, cyclobutyl, cyclopentyl, cyclopentenyl, cyclohexyl, cyclohexenyl and cycloheptyl. $C_{3-7}$cycloalkyl additionally includes a cycloheptyl ring.

Ⓝ as used herein indicates a nitrogen heterocycle, which may be a saturated or unsaturated stable five-, six- or seven-membered monocyclic ring, containing up to three nitrogen atoms or containing one nitrogen atom and a heteroatom chosen from oxygen and sulfur, and which may be substituted on any atom that results in a stable structure. Representative of Ⓝ are pyrroline, pyrrolidine, imidazole, imidazoline, imidazolidine, pyrazole, pyrazoline, pyrazolidine, piperidine, piperazine, morpholine, pyridine, tetrahydropyridine, tetrahydro- and hexahydro-azepine. In particular, Ⓝ may be pyrolidinyl, piperidinyl or tetrahydropyridinyl.

t-Bu refers to the tertiary butyl radical, Boc refers to the t-butyloxycarbonyl radical, Fmoc refers to the fluorenylmethoxycarbonyl radical, Ph refers to the phenyl radical, Tet refers to 5-tetrazolyl, Cbz refers to the carbobenzyloxy radical, BrZ refers to the o-bromobenzyloxycarbonyl radical, Ac refers to acetyl, Nph refers to 1- or 2-naphthyl, chex refers to cyclohexyl, Abu refers to 2-amino butyric acid, APmp refers to 2-amino-3,3-cyclopentamethylene-3-mercaptopropionic acid, Dtc refers to 5,5-dimethylthiazolidine-4-carboxylic acid, Nle refers to norleucine, Pen refers to L-penicillamine or β,β dimethyl cysteine, Tpr refers to thiazolidine-4-carboxylic acid, Nal refers to naphthylalanine, BOP refers to benzotriazol-1-yloxytris-(dimethylamino)phosphoniumhexafluorophosphate, DCC refers to 1,3-dicyclohexyl-carbodiimide, DMAP refers to 4-dimethylaminopyridine, DIEA refers to diisopropylethyl amine, EDC refers to N-ethyl-N' (dimethylaminopropyl)-carbodiimide, HOBt refers to 1-hydroxybenzotriazole, NMM refers to 4-methylmorpholine, THF refers to tetrahydrofuran, DMF refers to dimethyl formamide, HF refers to hydrofluoric acid and TFA refers to trifluoroacetic acid.

Generally the compounds of the formula (I) are prepared by a process which comprises reacting a compound of the formula (II):

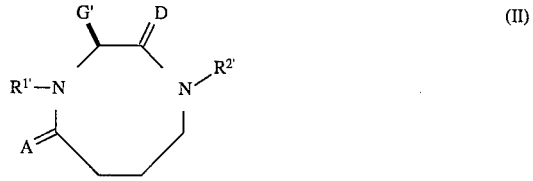

wherein $R^{1'}$ is $R^1$ or $R^1$ in which any reactive groups are protected, $R^{2'}$ is $R^2$ or $R^2$ in which any reactive groups are protected, G' is G in which any reactive groups are protected, with a deprotecting reagent.

Typical protecting groups for specific functional groups, and methods of removing them, are well known in the art, and are disclosed, for instance in Greene et al., PROTECTIVE GROUPS IN ORGANIC SYNTHESIS, Second Edition, John Wiley and Sons, New York (1991).

As is common in the chemical and peptide arts, reactive functionalities which may be incompatible with certain reaction conditions are often protected during the synthesis. Reactive groups which may be optionally protected include carboxylic or sulfonic acid, hydroxyl, amino, thio, guanidino and imidazole functionalities. Acids are normally protected by forming aryl, aralkyl or aliphatic esters, such as C1-6alkyl, phenyl, naphthyl or benzyl esters, and are deprotected by conventional methods of hydrolysis, such as with acid or an alkali hydroxide, or hydrogenation. Methyl, cyclohexyl and benzyl esters are particularly useful. The hydroxyl group is commonly protected as an ether, particularly a silyl ether, or as an ester. Tetrahydropyranyl-, trimethylsilyl, t-butyldiphenylsilyl ethers and t-butyldimethylsilyl-ethers, and acetyl- and benzoyl-esters are representative protecting groups for the hydroxyl moiety. The Boc, Cbz or Fmoc group may be used for protection of an amino group. A benzyl group or suitably substituted benzyl group is used to protect the mercapto group. Alternatively, a mercapto group may be protected as a disulfide, such as with ethyl sulfide The imidazole group is commonly protected by a Boc or trimethylsilylethoxymethyl (SEM) group. The tosyl or nitro group may be used for protection of the guanidino group. Except for the Boc group, the protective groups are, most conveniently, those which are not removed by mild acid treatment. These protective groups are removed by such methods as catalytic hydrogenation, fluoride ion, sodium in liquid ammonia or hydrofluoric acid treatment, as known in the art. Hydrofluoric acid is a particularly useful deprotecting reagent.

A process for preparing a compound of the formula:

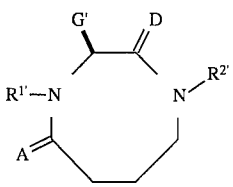
(II)

wherein, $R^{1'}$ is $R^1$, or protected $R^1$, $R^{2'}$ is $R^2$ or a protected $R^2$, $G'$ is a protected G, and A, D, $R^1$, G and $R^2$ are as defined in formula (I); which comprises,
1) cyclizing a compound of the formula

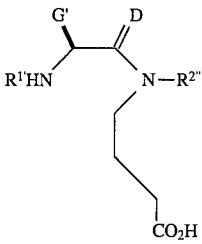
(III)

wherein, D, G' and $R^{1'}$ are as defined in formula (II), $R^{2''}$ is $R^{2'}$ or $(CH_2)_m(C=O)—OR^{11}$, $R^{11}$ is C1-6alkyl or $(CH_2)Ar$ and m is 1 or 2, or
cyclizing a compound of the formula:

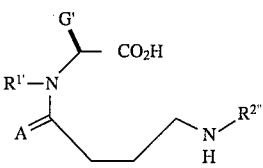

where in A, G', $R^{1'}$, and $R^{2''}$ are as defined for formula (II), and 2) thereafter, if $R^{2'}$ is $(CH_2)_m(C=O)—OR^{11}$, hydrolyzing the ester to the acid, and reacting the acid with a compound of the formula:

$$H—Q—CH(R^{3''})(R^{4''}) \qquad (V)$$

and a coupling reagent, wherein, Q is NH or O, $R^{3'}$ is $R^3$, as defined in formula (I), or a protected $R^3$. Suitably $R^{1'}$ is H, Boc, $R^6CO$ or methyl, $R^{3'}$ is $CO_2Bzl$, $R^{4'}$ is $CO_2CH_3$ or $CONHAr$, and G' is $(CH_2)_tNHC(=NH)NH—Tos$. BOP and DPPA are especially useful coupling reagents.

A particularly useful intermediate is the compound (VI):

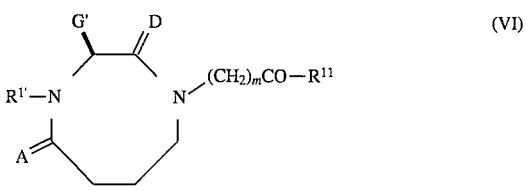

wherein A, D, G' and $R^{1'}$ are as defined for formula (II), which is prepared by either cyclization process when $R^{2''}$ is $(CH_2)_m(C=O)—OR^{11}$.

The compounds (III) and (IV) are available using conventional techniques and commercially available reagents, as illustrated more fully herein. Typically, N-alkylation of an amino acid, such as Gly, with a radical which can be converted to a 4-carboxy butanoic acid or ester, provides a simple intermediate. This intermediate can be converted to a compound of formula (III) by coupling the carboxyl group of an amino acid, such as arginine to the glycyl amino group; or to a compound of formula (IV) by coupling the amino group of a suitably substituted amino acid, such as arginine, to the carboxyl group of the butanoic acid moiety. Alternately, reductive amination of an N-(butyraldehyde)glycyl intermediate with a suitably substituted α-amino acid provides compounds of formula (III).

The following schemes illustrate the method of preparing compounds of this invention. Schemes 1 and 3 illustrate the method of preparation via cyclization of a compound of formula (IV). Scheme 1 illustrates the method for compounds wherein A is (H,H) and D is O; and scheme 3 illustrates the method wherein both A and D are O.

Schemes 4 and 7 illustrate the method of preparation via cyclization of a compound of formula (III). Scheme 7 illustrates alternate methods of effecting the cyclization of compounds, which may be applied to either compound (III) or (IV).

Scheme 2 illustrates a method for varying the group $R^{1'}$.

Schemes 5 and 6 illustrate the method of hydrolysis of a compound of formula (VI) and its reaction with a coupling reagent and a compound of formula (V).

Scheme 1

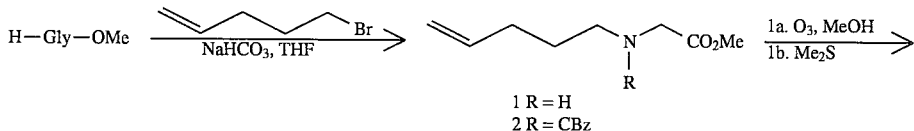

-continued
Scheme 1
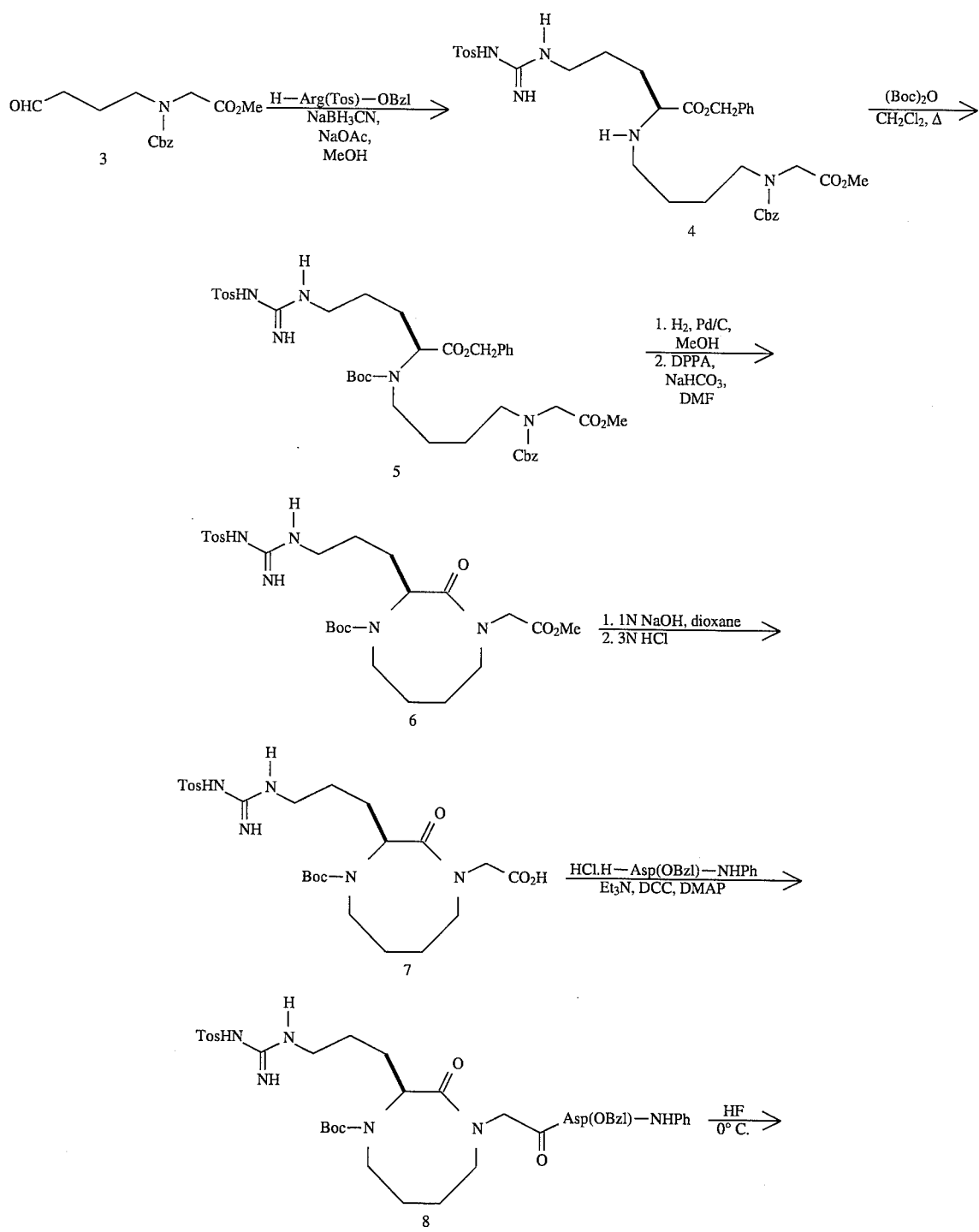

11
12
-continued
Scheme 1
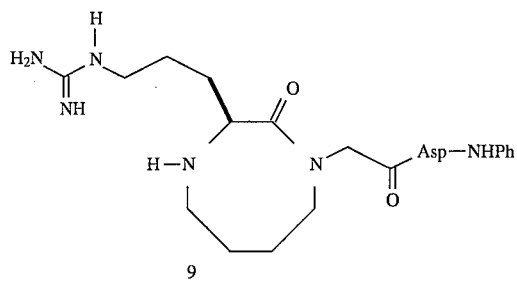
Scheme 2
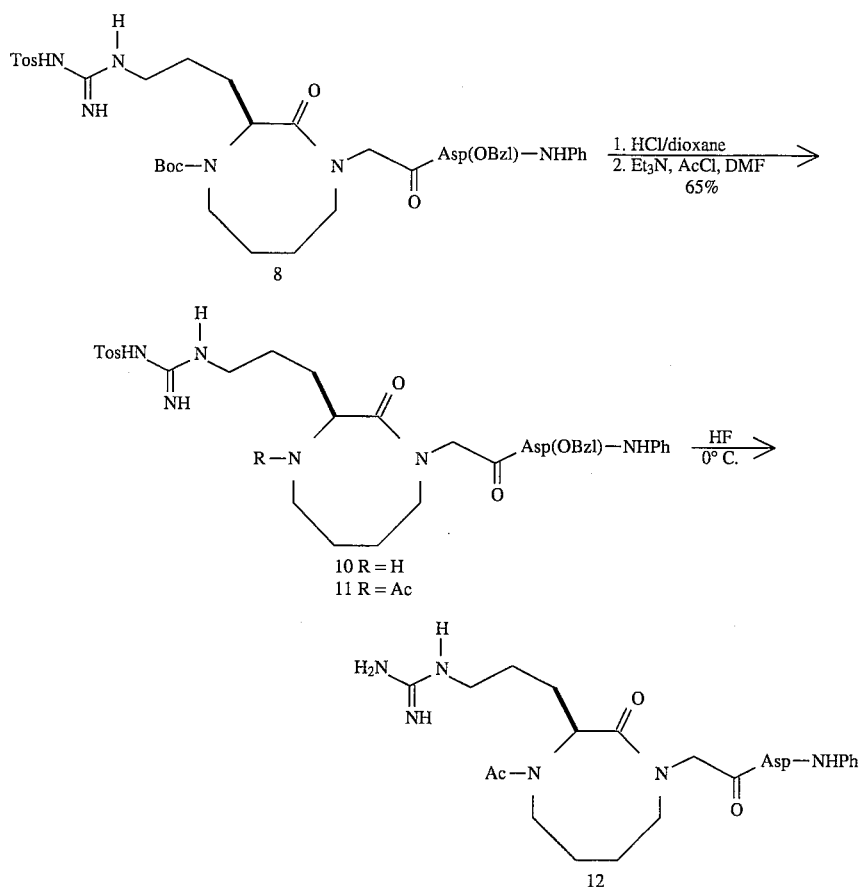
Scheme 3
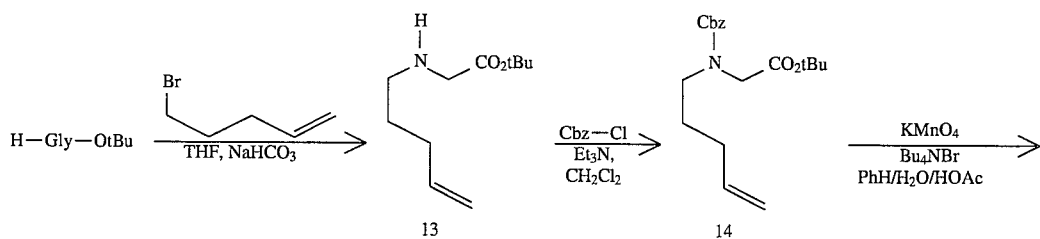

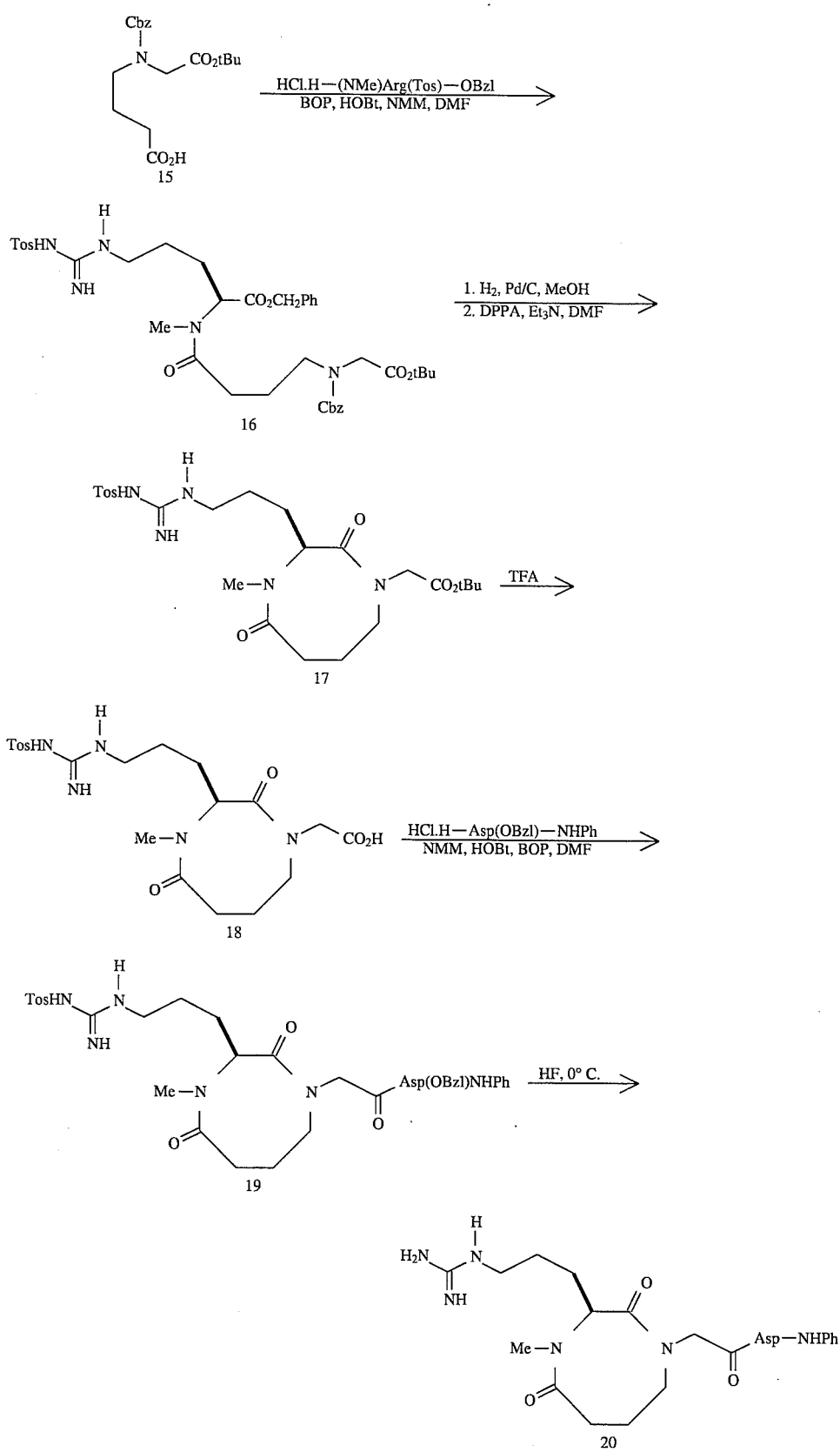

Scheme 4
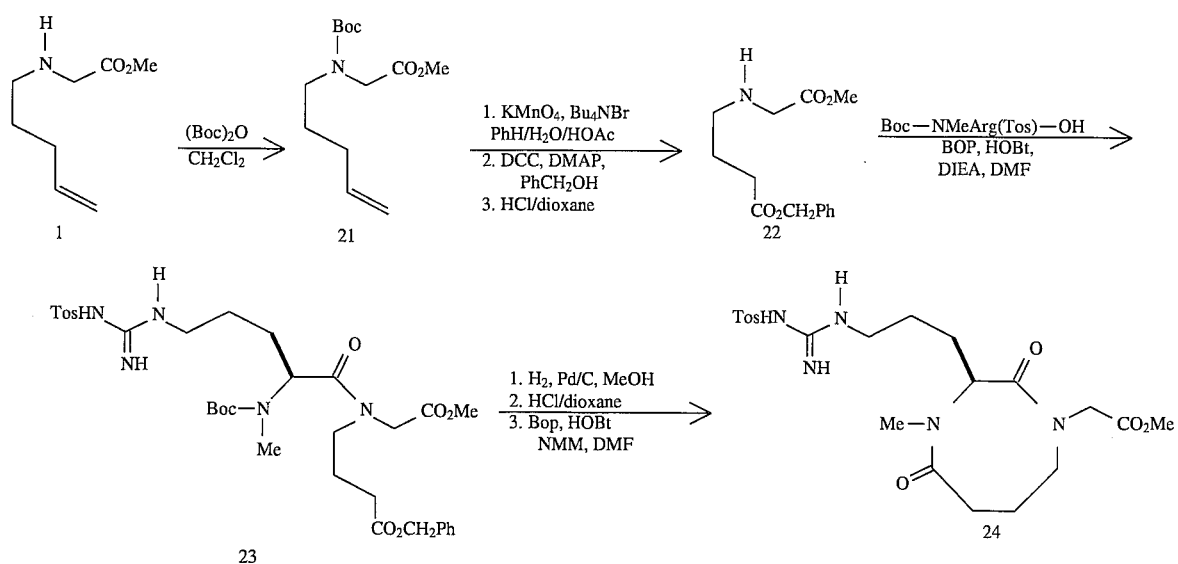
Scheme 5
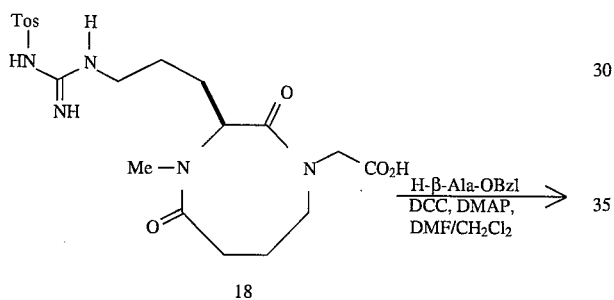
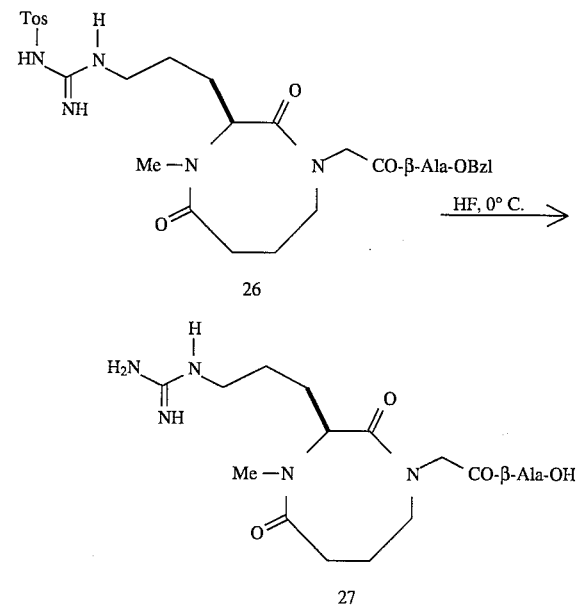
Scheme 6
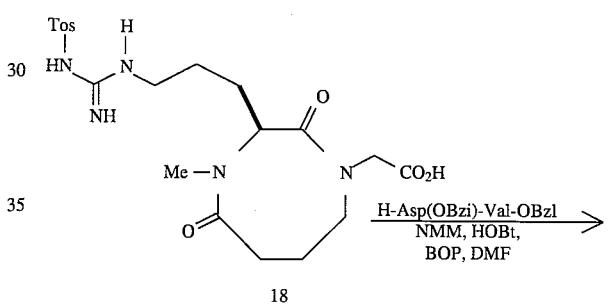

Scheme 7

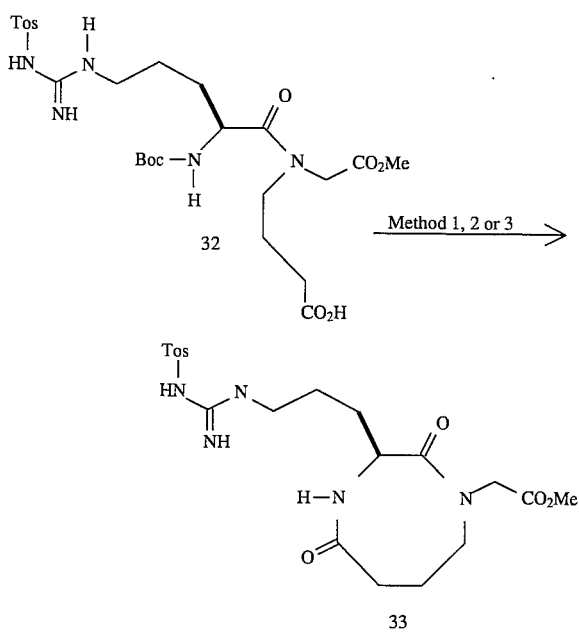

1. $C_6Cl_5$—OH, DCC; HCl/dioxane; DMF, DIEA
2. HCl/dioxane; DPPA, DIEA, $NaHCO_3$, DMF
3. HCl/dioxane; BOP, HOBt, NMM, DMF The moiety Y is a generally a basic functional group, such as an amino, guanidino, amidino or heterocyclic group, which is protected during the synthesis. Typically, this group is prepared as a functional group on the side chain of an α-amino acid. For example, compounds wherein Y is a suitably substituted R'R"N—, R"R'NC(—NR'), $R'_2N(R^{13})C=N$—, $R"N=(R^{13})C$—NR'—, $R'_2N(R'_2N)C=N$— or R"R'N(R'N=)C—NR', are prepared by conventional methods including those disclosed in EP-A 0 372 486, EP-A 0 381 033 or EP-A 0 478 363, which are incorporated herein by reference.

Compounds wherein Y is Ⓝ are prepared, inter alia, by methods disclosed in EP-A 0 478 363.

Compounds wherein Y is $R'_2N(R'_2N)C=N$—X— or R"R'N(R'N=)C—NR'—X—, and X is O are prepared, inter alia, by methods disclosed in *J. Org. Chem.*, 51, 5047 (1986).

Compounds wherein Y is $R'_2N(R'_2N)C=N$—X— or R"R'N(R'N=)C—NR'—X—, and X is N=CR', are prepared, inter alia, by methods disclosed in U.S. Pat. No. 3,714,253 and *Eur. J. Med. Chem.-Chim. Ther.*, 20, 25 (1985).

Compounds wherein Y is $R'_2N(R'_2N)C=N$—X— or R"R'N(R'N—)C—NR'—X—, and X is C(O), are prepared, inter alia, by methods disclosed in U.S. Pat. No. 3,714,253 and *Can. J. Chem.*, 43, 3103 (1965).

Compounds wherein Y is R'ONR'C(=NR')— may be prepared, inter alia, by methods disclosed in *J. Het. Chem.*, 16, 1063 (1979) or *J. Het. Chem.*, 26, 125 (1989).

Compounds wherein Y is $R'_2NR'NC$ (=NR')— are prepared by conventional methods including those disclosed in Syn., 583 (1974).

Compounds wherein Y is R'R"NR'N— are prepared, inter alia, by methods disclosed in *J. Prakt. Chem.*, 36, 29 (1967).

Compounds wherein Y is R'R"NR'NCO— are prepared, inter alia, by methods disclosed in *Bull. Chem. Soc. Jpn.*, 43, 2257 (1970).

Compounds wherein Y is R"R'NC(=NR')Y, and Y is S, are prepared, inter alia, by methods disclosed in *Chem. Lett.*, 1379 (1986).

Compounds wherein Y is R"R'NC (=NR')Y and Y is O, are prepared by conventional methods including those disclosed in Japanese Patent 2022751.

Acid addition salts of the compounds are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention provides a pharmaceutical composition which comprises a compound according to formula (II) and a pharmaceutically acceptable carrier. Pharmaceutical compositions of the compounds of this invention may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or nonaqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

This invention also provides a method of inhibiting platelet aggregation and clot formation in a mammal, especially a human, in need thereof, which comprises the internal administration of a compound according to formula (II) and a pharmaceutically acceptable carrier. Indications for such therapy include myocardial infarction, deep vein thrombosis, pulmonary embolism, dissecting anurysm, transient ischemia attack (TIA), stroke and other infarct-related disorders. Chronic or acute states of hyper-aggregability, such as disseminated intravascular coagulation (DIC), septicemia, surgical or infectious shock, post-operative and postpartum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the compounds of this invention may be used in a method for the prevention of metastatic conditions.

The compounds of this invention are administered either orally or parenterally to the patient, in a manner such that the concentration of drug in the plasma is sufficient to inhibit platelet aggregation. The pharmaceutical composition containing the compound is administered at a dose between about 0.2 to about 50 mg/kg in a manner consistent with the condition of the patient. For acute therapy, parenteral administration is preferred. For persistent states of hyperaggregability, an intravenous infusion of the compound in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The compound is administered one to four times daily at a level of about 0.4 to about 50 mg/kg. to achieve a total daily dose of about 0.4 to about 200 mg/kg/day.

This invention further provides a method for inhibiting the reocclusion of an artery or vein following fibrinolytic therapy, which comprises internal administration of an effective amount of a compound according to formula (II) and a fibrinolytic agent to a mammal in need thereof. Administration of a compound of this invention in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334 and in GB 8815135.2. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592 (U.S. Ser. No. 890,432), German Patent Application No. 3032606, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compounds of this invention and fibrinolytic agent in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The compound of this invention is administered just prior to, at the same time as, or just after parenteral administration of tPA or other fibrinolytic agent. It may prove desirable to continue treatment with the compounds of this invention for a period of time well after reperfusion has been established to maximally inhibit post-therapy reocclusion. The effective dose of tPA, SK, UK or pUK may be from 0.1 to 5 mg/kg and the effective dose of the compounds of this invention may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials, ampoules or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and a compound of this invention may be packaged separately, as in two containers, or lyophilized together as a powder and provided in a single container.

When both agents are provided in solution form, they can be contained in an infustion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of a compound of this invention followed by an infusion of the fibrinolytic agent.

The pharmacological activity of the peptides was assessed by the following tests:

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandin*, 19, 629–43 (1980).

Inhibition of Platelet Aggregation

Blood was collected (citrated to prevent coagulation) from, naive, adult mongrel dogs. Platelet rich plasma, PRP, was prepared by centrifugation at 150×g for 10 min at room temperature. Washed platelets were prepared by centrifuging PRP at 800×g for 10 min. The cell pellet thus obtained was washed twice in Tyrode's buffer (pH 6.5) without $Ca^{++}$ and resuspended in Tyrode's buffer (pH 7.4) containing 1.8 mM $Ca^{++}$ at $3\times10^5$ cells/mL. Peptides were added 3 min. prior to the agonist in all assays of platelet aggregation. Final agonist concentrations were 0.1 unit/mL thrombin and 2 mM ADP (Sigma). Aggregation was monitored in a Chrono-Log Lumi-Aggregometer. Light transmittance 5 min after addition of the agonist was used to calculate percent aggregation according to the formula % aggregation=[(90-CR)+(90−10)]×100, where CR is the chart reading, 90 is the baseline, and 10 is the PRP blank reading. $IC_{50}$'s were determined by plotting [% inhibition of aggregation] vs. [concentration of peptide]. Peptides were assayed at 200 mM and diluted sequentially by a factor of 2 to establish a suitable dose response curve.

To assess the stability of the peptide to plasma proteases, the peptides were incubated for 3 h (rather than 3 min) in the PRP prior to addition of the agonist.

The compounds of this invention showed $IC_{50}$'s for the aggregation of dog platelets stimulated by ADP of between about 0.1 and 200 μM. The $IC_{50}$ of compound (12) of Example 2 was 0.17 μM.

The examples which follow are intended to in no way limit the scope of this invention, but are provided to illustrate how to make and use the compounds of this invention. Many other embodiments will be readily apparent and available to those skilled in the art.

EXAMPLES

In the examples which follow all temperatures are in degrees Celsius. NMR were performed at 90 MHz with a EM390 spectrometer or at 250 MHz with a Bruker AM250 spectrometer. Chemical shifts are reported in δ units from the internal standard tetramethylsilane. Analtech silica gel GF and EM silica gel thin layer plates were used for thin layer chromatography. Both flash and gravity chromatography were carried out on Merck 60 (230–400 mesh) silica gel. ODS refers to an octadecylsilyl derivatized silica gel chromatographic support. 5μ Apex-ODS indicates an octadecylsilane derivatized silica gel support, having a nominal particle size of 5μ, made by Jones Chromatography, Littleton, Colorado. Teflon® is poly-tetrafluoroethylene and is a registered trademark of the Dupont Co., Wilmington, Del. Celite® is filter aid composed of acid washed diatomaceous silica, and is a registered trademark of Mansville Corp., Denver, Col.

Preparation of Amino Acid Intermediates

The following amino acid derivatives were purchased commercially: t-butyl glycinate, methyl glycinate hydrochloride and N-t-butoxycarbonyl-β-alanine (Schweizerhall/Chemical Dynamics Corp, South Plainfield, N.J.); $N^\gamma$-tosyl-$N^\alpha$-t-butyloxycarbonyl-arginine, N-t-butoxycarbonyl-γ-benzyl aspartic acid (Peninsula Laboratories, Belmont, Calif.), and $N^\gamma$-tosyl-$N^\alpha$-methyl-$N^\alpha$-t-butyloxycarbonyl-arginine (Bachem Biosciences, Inc., Philadelphia, Penna.).

Preparation of benzyl-$N^\gamma$-tosyl-arginate hydrochloride $N^\gamma$-Tosyl-$N^\alpha$-t-butyloxycarbonyl-arginine (33 g, 77 mmol) was dissolved in methanol and the resulting solution diluted with water until just prior to precipitation. Solid cesium bicarbonate was added until the pH of the solution was 7.0. The reaction mixture was evaporated at reduced pressure and the residue evaporated two times from toluene to give the cesium salt of the acid. This salt was dissolved in dimethylformamide and treated with benzyl bromide (13.8 mL, 115.5 mmol) and the resulting mixture was heated at 45° C. for 24 h. The solvent was evaporated under high vacuum and the residue purified by flash chromatography (silica gel, 75% ethyl acetate/hexane) to yield benzyl $N^\gamma$-tosyl-$N^\alpha$-t-butyloxycarbonyl-argininate (29.05 g, 80%): $^1$H NMR (CDCl$_3$) ε 1.38 (s, 9H), 1.38–1.83 (m, 4H), 2.35 (s, 3H), 2.97–3.35 (m, 2H), 4.02–4.40 (m, 1H), 5.17 (s, 2H), 5.35 (d, 1H, J=8.3 Hz), 6.42 (br s, 3H), 7.35 (s, 5H), 7.50 (q, 4H).

Benzyl $N^\gamma$-tosyl-$N^\alpha$-t-butyloxycarbonyl-argininate (29.1 g, 56 mmol) was treated with 4N HCl in dioxane (200 mL) and stirred at room temperature for 2 h. The reaction mixture was then evaporated at reduced pressure and the residue was evaporated two times from toluene to give crude benzyl $N^\gamma$-tosyl-argininate hydrochloride which was used without further purification.

Preparation of Benzyl $N^\gamma$-methyl-$N^\alpha$-t-butyloxy-carbonyl-arginate $N^\gamma$-Tosyl-$N^\alpha$-methyl-$N^\alpha$-t-butyloxycarbonyl-arginine (5.39 g, 12.2 mmol) was dissolved in methanol and the resulting solution was diluted with water until just prior to precipitation. Solid cesium bicarbonate was added until the pH of the solution was 7.0. The reaction mixture was evaporated at reduced pressure, the residue was evaporated from toluene (2x), and dried under high vacuum to give the cesium salt of the acid. This salt was then dissolved in dimethylformamide (250 mL) and treated with benzyl bromide (1.89 mL, 15.9 mmol). The resulting solution was heated at 45° C. for 72 h. The solvent was evaporated under high vacuum and the residue dissolved in ethyl acetate, washed with water dried over anhydrous MgSO$_4$, filtered and evaporated at reduced pressure. The residue was purified by flash chromatography (silica gel, 70% ethyl acetate/hexane) to yield (4.82 g, 74%) of benzyl $N^\gamma$-tosyl-$N^\alpha$-methyl-$N^\alpha$-t-butyloxycarbonyl-argininate:

$^1$H NMR (CDCl$_3$) ε 1.38 (s, 9H), 1.38–1.83 (m, 4H), 2.35 (s, 3H), 2.97–3.35 (m, 2H), 4.02–4.40 (m, 1H), 5.17 (s, 2H), 5.35 (d, 1H, J=8.3 Hz), 6.42 (br s, 2H), 7.30 (br s, 1H), 7.35 (s, 5H), 7.50 (q, 4H).

Benzyl-$N^\gamma$-tosyl-$N^\alpha$-methyl-$N^\alpha$-t-butyloxycarbonyl-argininate (2.10 g, 3.94 mmol) was treated with 4N HCl in dioxane at room temperature for 3 h. The reaction mixture was then evaporated at reduced pressure and the residue was evaporated two times from toluene and dried under high vacuum to give crude benzyl $N^\gamma$-tosyl-$N^\alpha$-methyl-argininate hydrochloride which was used without further purification.

Preparation of N-t-butyoxycarbonyl-aspartylanilide γ-benzyl ester

N-t-Butyoxycarbonyl-aspartic acid γ-benzyl ester (5.0 g, 15.5 mmol) in dimethylformamide (100 mL) was treated with aniline (2.1 mL, 23.3 mmol), lhydroxybenzotriazole (2.3 g, 17.1 mmol) and N, N-dicyclohexylcarbodiimde (3.2 g, 15.5 mmol) and the resulting solution was stirred at room temperature for 96 h. The reaction mixture was filtered and evaporated. The residue was purified by flash chromatography (silica gel, 15% ethyl acetate/hexane) to give N-t-butyoxycarbonylaspartylanilide γ-benzyl ester (5.28 g, 85%). $^1$H NMR (CDCl$_3$) ε 1.45 (s, 9H), 2.60–3.23 (m, 2H), 4.53–4.87 (m, 1H), 5.20 (s, 2H), 5.90 (d, 1H, J=9 Hz), 7.00–7.67 (m, 5H), 7.40 (s, 5H), 8.63 (br, 1H).

N-t-Butyoxycarbonyl-aspartylanilide γ-benzyl ester (2.90 g, 10 mmol) was treated with 4N HCl in dioxane (30 mL) at room temperature for 2 h. The solution was evaporated at reduced pressure and the residue was evaporated two times from toluene and then from methanol and the resulting crude γ-benzyl aspartyl anilide hydrochloride was dried under vacuum and used without further purification in the subsequent coupling reaction.

EXAMPLE 1

Preparation of N-[2-Oxo-3-(S)-[3-guanidinopropyl]-octahydro-1,4-diazocin-1-yl]-acetyl-aspartyl-1-phenylamide (9)

a) methyl N-carbobenzyloxy-N-5-[pent-1-enyl]-glycinate (2).

Methyl glycinate hydrochloride (25.0 g, 199 mmol) in tetrahydrofuran (400 mL) was treated with triethylamine (28.0 mL, 200 mmol) at room temperature followed by sodium bicarbonate (16.7 g, 200 mmol) and 5-bromo-pent-1-ene (28.5 mL, 240 mmol). The subsequent mixture was heated at reflux with mechanical stirring for 18 h. The reaction mixture was cooled to room temperature, diluted with ethyl acetate and washed with water. The combined organic extracts were dried over anhydrous $MgSO_4$, filtered and evaporated at reduced pressure to give crude methyl N-5-[pent-1-enyl]glycinate (1) which was used without further purification. Compound 1: $^1$H NMR ($CDCl_3$) ε 1.33–1.80 (m, 3H), 2.10 (q, 2H, J =7.5 Hz), 2.63 (t, 2H, J=7.5 Hz), 3.42 (s, 2H), 3.75 (s, H), 4.87–5.73 (m, 2H), 5.50–6.17 (m, 1H).

Methyl-N-5-[pent-1-aryl]-glycinate (1) was dissolved in methylene chloride (300 mL) and cooled to 0° C. Triethylamine (28 mL, 200 mmol) and benzyl chloroformate (28.6 mL, 200 mmol) were added and the solution was stirred at room temperature for 18 h. The reaction mixture was washed with 5% sodium bicarbonate (aqueous), 3N HCl and 1N HCl, dried over anhydrous $MgSO_4$, filtered and evaporated at reduced pressure. The residue was purified using flash chromatography (silica gel, 10–20% ethyl acetate/hexane) to yield the title compound (2). (14.03 g, 24%). Compound 2: $^1$H NMR ($CDCl_3$) ε 1.63 (p, 2H, J=7.5 Hz), 1.87–2.23 (m, 2H), 3.37 (t, 2H, J=7.5 Hz), 3.67/3.73 (2s, 3H), 3.97/4.03 (2s, 2H), 4.85–5.28 (m, 4H), 5.53–6.10 (m, 1H), 7.38 (s, 5H).

b) methyl N-carbobenzyloxy-N-4-[butan-1-al]-glycinate (3).

Compound (2) (14.04 g, 48.2 mmol) was dissolved in methanol (400 mL) and treated with a stream of ozone at −78° C. until the color of the solution turned blue (excess ozone present). The stream of ozone was then replaced with a stream of argon until the residual ozone was displaced. The reaction mixture was treated with methyl sulfide (13 mL) and warmed slowly to room temperature overnight. The reaction mixture was evaporated at reduced pressure and the residue was purified using flash chromatography (silica gel, 40% ethyl acetate/hexane) to yield the title compound (3) (11.19 g, 80%). Compound 3: $^1$H NMR ($CDCl_3$) ε 1.82 (p, 2H, J=7.5 Hz), 2.30–2.67 (m, 2H), 3.40 (t, 2H, J=7.5 Hz), 3.67/3.73 (2s, 3H), 4.00 (br s, 2H), 5.20 (br s, 2H), 7.40 (s, 5H), 9.78 (d, 1H, J=10.5 Hz).

c) benzyl $N^\gamma$-tosyl-$N^\alpha$-[4-[[N-[1-carboxylmethyl]-methyl]-N-carbobenzyloxy-amino]-butyl ]-argininate (4)

Benzyl $N^\gamma$-tosyl-argininate hydrochloride (56 mmol) was dissolved in methanol (200 mL) and treated with sodium acetate (4.59 g, 56 mmol). The resulting solution was stirred for 5 min. The reaction mixture was treated with methyl N-carbobenzyloxy-N-4-[butan-1-al]-glycinate (3) (11.19 g, 38.1 mmol) and sodium cyanoborohydride (2.40 g, 38.19 mmol) and stirred at room temperature for 20 h. The reaction mixture was then evaporated at reduced pressure. The residue was dissolved in ethyl acetate, washed with 5% sodium bicarbonate (aqueous), dried over anhydrous $MgSO_4$, filtered and evaporated at reduced pressure. Purification of the crude product by flash chromatography (silica gel, 2–4% methanol/chloroform) yielded the title compound (4) (20.57 g, 52%). Compound 4: $^1$H NMR ($CDCl_3$) ε 1.23–1.87 (m, 9H), 2.07– 2.70 (m, 5H), 2.87–3.50 (m, 5H), 3.67 (br s, 3H), 3.97 (s, 2H), 5.13 (s, 4H), 6.18–6.77 (m, 2H), 6.96–8.13 (m, 15H).

d) benzyl $N^\gamma$-tosyl-$N^\alpha$-t-butyloxycarbonyl-$N^\alpha$-[4-[[N-[1-carboxylmethyl]-methyl]-N-carbobenzyloxy-amino]-butyl] argininate (5)

Compound (4) (20.57 g, 29 mmol) was dissolved in methylene chloride and treated with di-tert-butyl dicarbonate (12.6 g, 58 mmol). The resulting solution was heated at 45° C. for 72 h. The reaction mixture was evaporated at reduced pressure and the residue purified by flash chromatography (silica gel, 2% methanol/chloroform) to yield the title compound (5) (18.66 g, 80%). Compound 5: $^1$H NMR ($CDCl_3$) ε 1.23–2.10 (m, 17 H), 2.35 (s, 3H), 2.70–3.50 (m, 6H), 3.68 (br s, 3H), 3.95 (s, 2H), 4.00–4.43 (m, 1H), 5.13 (s, 4H), 5.85–6.63 (m, 3H), 7.35 (s, 10H), 7.50 (q, 4H).

e) methyl N-[2-oxo-3-(S)-[3-[$N^\gamma$-tosyl]-guanidinopropyl]-4-t-butyloxycarbonyl-octahydro -1,4-diazocin-1-yl]-acetate (6)

Compound (5) (8.38 g, 10.5 mmol) was dissolved in methanol with 10% Pd on carbon (833 mg), and the resulting reaction mixture was treated with hydrogen in a Parr apparatus until hydrogen uptake ceased. The catalyst was filtered through a bed of Celite® and the filtrate was evaporated at reduced pressure. The resulting amino acid was dissolved in dimethylformamide (1600 mL) and cooled to 0° C. Solid sodium bicarbonate (4.41 g, 52.5 mmol) and diphenylphosphoryl azide (4.52 mL, 21 mmol) were added and the reaction warmed slowly to room temperature and stirred for 2 days. The reaction mixture was evaporated under high vacuum and the residue purified twice by flash chromatography (silica gel, 3% methanol/chloroform) to yield the title compound (6) (2.3 g, 37%) (6). Compound 6: $^1$H NMR ($CDCl_3$) ε 1.32–2.30 (m, 8H). 1.47 (s, 9H), 2.40 (s, 3H), 2.83–3.50 (m, 4H), 3.57–4.42 (m, 4H). 3.75 (s, 3H), 4.75 (br s, 1H), 6.40 (br s, 3H), 7.53 (AB, 4H); MS (DCI/$NH_3$) m/e 554 (M+H)$^+$.

f) N-[2-oxo-3-(S)-[3-[$N^\gamma$-tosyl]guanidimopropyl]-4-t-butyloxycarbonyl -octahydro-1,4-diazocin-1-yl]-acetic acid (7)

Compound (6) (1.1 g, 2.0 mmol) was dissolved in dioxane (10 mL) and treated with 3 mL of 1N NaOH at room temperature for 3 h. The reaction mixture was acidified (pH=2) with 3N HCl and evaporated under vacuum. The residue was evaporated twice from a mixture of toluene and chloroform to give crude title compound (7), which was used without further purification.

g) N-[2-oxo-3-(S)-[3-[$N^\gamma$-tosyl]-guanidinopropyl]-4-t-butyloxycarbonyl-octahydro -1,4-diazocin-1-yl]acetyl-γ-benzyl-aspartyl-1-phenylamide (8)

Compound (7), dissolved in dimethylformamide, was treated with the γ-benzyl aspartyl anilide hydrochloride (1.0 g, 3.0 mmol) and triethylamine (278 μL, 2.0 mmol) followed by 1-hydroxybenzotriazole (297 mg, 2.2 mmol) and N,N-dicylcohexylcarbodiimide (412 mg, 2.0 mmol). The resulting solution was stirred at room temperature for 18 h. After evaporation under high vacuum, the residue was purified by flash chromatography (silica gel, 2% methanol/chloroform) to yield the title compound (8) (480 mg, 30%). Compound 8: $^1$H NMR (CDCl$_3$) ε 1.30–2.13 (m, 8H), 1.45 (s, 9H), 2.33 (s, 3H), 2.73–4.13 (m, 10H), 4.63–5.23 (m, 2H), 5.17 (s, 2H), 6.27 (br s, 2H), 6.63–7.93 (m, 16H), 9.00 (s, 1H); MS (FAB) m/e 820 (M+H)$^+$.

h) N-[2-Oxo-3-(S)-[3-guanidinopropyl]-octahydro-1,4-diazocin-1-yl]-acetyl-aspartyl-1-phenylamide (9)

Compound (8) (363 mg, 0.443 mmol) was transfered to a Teflon® reaction vessel in methylene chloride. The solvent was evaporated using a stream of argon. The residue was treated with anhydrous HF (10 mL) at 0° C. for 1 h. After the HF was removed under vacuum, the residue was dissolved in 1% aqueous acetic acid and lyophilized. A portion of the crude product was purified by reverse phase hplc [5 μ Apex-ODS, 10×250 mm column; 4.0 mL/min; 77:23 water-0.1% trifluoroacetic acid:acetonitrile-0.1% trifluoroacetic acid] to yield, after lyophilization from 1% aqueous acetic acid, the title compound (26 mg). Compound 9: MS(FAB) m/e 476 [M+H]$^+$; HPLC k' 2.46 [5 μ Apex-ODS, UV detection at 220 nm, 80:20 water-0.1% trifluoroacetic acid:acetonitrile-0.1% trifluoroacetic acid]; HPLC k' 3.92 [5μ Apex-ODS, UV detection at 220 nm, gradient elution, A: water-0.1% trifluoroacetic acid, B: acetonitrile-0.1% trifluoroacetic acid, 5–50% B during 20 min.] TLC R$_f$ 0.10 (silica gel, 4:1:1 butanol:acetic acid:water); TLC R$_f$ 0.35 (silica gel, 1:1:1:1 butanol:acetic acid:water:ethyl acetate).

EXAMPLE 2

Preparation of N-[2-Oxo-3-(S)-[3-guanidinopropyl]-4-acetyl-octahydro-1,4-diazocin- 1-yl ]-acetyl-aspartyl-1-phenylamide a) N-[2-oxo-3-(S)-[3-[N$^\gamma$-tosyl]-guanidinopropyl]-octahydro-1,4-diazocin-1-yl]-acetyl-γ-benzyl-aspartyl-1-phenylamide hydrochloride (10)

Compound (8) (652 mg, 0.796 mmol) was treated with 4N HCl in dioxane (75 mL) at room temperature for 2 h. The reaction mixture was then evaporated at reduced pressure and the residue evaporated twice from toluene and dried under vacuum to give the crude title compound (10), which was used without further purification.

b) N- [2-oxo-3-(S)-[3-[N$^\gamma$-tosyl]-guanidinopropyl]-4-acetyl-octahydro-1,4-diazocin -1-yl]-acetyl-y-benzyl-aspartyl-1-phenylamide (11 )

Compound (10) (590 mg, 0.804 mmol) was dissolved in dimethylformamide (30 mL) and treated with triethylamine until the solution was neutral to moist pH paper. Acetyl chloride (114 μL, 1.61 mmol) was added, the pH of the solution was adjusted to ca. 8 using triethylamine, and the reaction was stirred at room temperature for 48 h. The reaction mixture was evaporated under vacuum and the residue was purified by flash chromatography (silica gel, 4–6% methanol/chloroform) to yield the title compound (11) (400 mg, 65%). Compound 11: MS (FAB) m/e 762 (M+H)$^+$.

c) N- [2-Oxo-3-(S)-[3-guanidinopropyl]-4-acetyl-octahydro-1,4-diazocin-1-yl]acetyl-aspartyl-1-phenylamide (12)

Compound (11) (200 mg, 0.262 mmol) was transfered to a Teflon® reaction vessel in methylene chloride, and the solvent was evaporated using a stream of argon. The residue was treated with anhydrous HF (10 mL) at 0° C. for 1 h. After all of the HF was removed under vacuum, the residue was dissolved in 1% aqueous acetic acid and lyophilized. A portion of the crude product (40 mg) was purified by reverse phase hplc [5 μ Apex-ODS, 10×250 mm column; 4.0 mL/min; 80:20 water-0.1% trifluoroacetic acid:acetonitrile-0.1% trifluoroacetic acid] to yield, after lyophilization from 1% aqueous acetic acid, the title compound (22.1 mg). Compound 12: MS(FAB) m/e 518 [M+H]$^+$; HPLC k' 2.55 [5μ Apex-ODS, UV detection at 220 nm, 78:22 water-0.1% trifluoroacetic acid:acetonitrile-0.1% trifluoroacetic acid]; HPLC k' 9.87 [5μ Apex-ODS, UV detection at 220 nm, gradient elution, A: water-0.1% trifluoroacetic acid, B: acetonitrile-0.1% trifluoroacetic acid, 5–50% B during 20 min]; TLC Rf 0.17 (silica gel, 4:1:1 butanol:acetic acid:water); TLC R$_f$ 0.53 (silica gel, 1:1:1:1 butanol:acetic acid:water:ethyl acetate).

EXAMPLE 3

Preparation of N-[2,5-dioxo-3-(S)-[3-guanidinopropyl]-4-methyl-octahydro-1,4-diazocin-1-yl]-acetyl-aspartyl-1-phenyl]amide (20 )

a) t-butyl N-5-[pent-1-enyl]-glycinate (13)

t-Butyl glycinate (10.1 g, 77.3 mmol) and 5-bromopent-1-ene (11 mL, 92.8 mmol) were dissolved in dry tetrahydrofuran (150 mL) and the resulting solution was heated at reflux over solid sodium bicarbonate (7.8, 92.8 mmol) for 24 h. The reaction mixture was diluted with water and extracted twice with ethyl acetate. The combined organic extracts were dried over anhydrous MgSO$_4$, filtered and evaporated at reduced pressure. The residue was purified using flash chromatography (silica gel, 30% ethyl acetate/hexane) to yield the title compound (13) (8.45 g, 55%). Compound 13: $^1$H NMR (CDCl$_3$) ε 1.08 (s, 1H), 1.47 (s, 9H), 1.57 (p, 2H, J=7.5 Hz), 1.93–2.28 (m, 2H), 2.60 (t, 2H, J=7.5 Hz), 3.30 (s, 2H), 4.88–5.20 (m, 2H), 5.63–6.13 (m, 1H); MS (DCl/NH$_3$) m/e 200 (M+H)$^+$.

b) t-butyl N-carbobenzyloxy-N-5-[pent-1-enyl]-glycinate (14)

Compound (13) (8.45 g, 42.4 mmol) was dissolved in methylene chloride (200 mL) and treated with triethylamine (7.1 mL, 51 mmol) and benzyl chloroformate (7.3 mL, 51 mmol). The resulting solution was stirred at room temperature for 72 h. The reaction mixture was diluted with chloroform, washed with 3N HCl (aqueous), dried over anhydrous MgSO$_4$, filtered and evaporated. The residue was purified using flash chromatography (silica gel, 10% ethyl acetate/hexane) to yield the title compound (14) (12.94 g, 92%). Compound 14: $^1$H NMR (CDCl$_3$) ε 1.40/1.45 (2s, 9H), 1.63 (p, 2H, J=7.5 Hz), 1.87–2.30 (m, 2H), 3.35 (t, 2H, J=7.5 Hz), 3.85/3.90 (2s, 2H), 4.87–5.30 (m, 3H), 5.50–6.17 (m, 1H), 7.38 (s, 5H); MS (DCl/NH$_3$) m/e 334 (M+H)$^+$.

c) t-butyl N-carbobenzyloxy-N-3-[1-carboxy-propanyl]-glycinate (15)

t-Butyl N-carbobenzyloxy-N-5-[pent-1-enyl]-glycinate (14) (4.16 g, 12.48 mmol) was dissolved in a 1:1 mixture of benzene and water (120 mL) and cooled to 0° C. Acetic acid (12 mL), tetra-n-butylammonium bromide (60 mg) and potassium permanganate (6.3 g, 40.2 mmol) were added at 0° C. After 15 min, the ice bath was removed and the reaction mixture stirred at room temperature for 3 h. The reaction mixture was then diluted with water and the excess potassium permanganate was quenched by the addition of solid sodium bisulfite. The reaction mixture was acidified with 1N HCl and extracted with ethyl acetate. The combined organic extracts were dried over anhydrous $MgSO_4$, filtered and evaporated at reduced pressure. The residue was purified using flash chromatography (silica gel, 98:2:0.1 chloroform-:methanol:acetic acid) to yield the title compound (15) (3.40 g, 78%). Compound 15: $^1$H NMR (CDCl$_3$) ε 1.38/1.43 (2s, 9H), 1.67–2.07 (m, 2H), 2.23–2.60 (m, 2H), 3.42 (t, 2H, J=6.8 Hz), 3.85/3.92 (2s, 2H), 5.17 (br s, 2H), 7.38 (s, 5H), 9.97 (br s, 1H).

d) benzyl $N^\gamma$-tosyl-$N^\alpha$-methyl-$N^\alpha$-[1-carboxy-3-[[N-[1-carboxylmethyl]-methyl]-N-carbobenzyloxy-amino]-propanyl]argininate (16)

Benzyl $N^\gamma$-tosyl-$N^\alpha$-methyl-argininate hydrochloride (2.1 g, 3.94 mmol) was dissolved in dimethylformamide (100 mL) and was treated with Compound (15) (1.51 g, 4.30 mmol), 4-methylmorpholine (2.84 mL, 25.8 mmol), 1-hydroxybenzotriazole (1.16 g, 8.6 mmol) and benzotriazol-1-yloxytris (dimethylamino) phosphonium hexafluorophosphate (3.8 g, 8.6 mmol). The resulting solution was stirred at room temperature for 48 h. The reaction mixture was evaporated under high vacuum and the residue was purified by flash chromatography twice (silica gel, 70% ethyl acetate/hexane; silica gel, 2% methanol/chloroform) to yield the title compound (16) (1.82 g, 60%) (16). Compound 16: $^1$H NMR (CDCl$_3$) ε 1.40 (br s, 9H), 1.60–3.73 (m, 16H), 2.35 (s, 3H), 3.85 (br s, 2H), 5.13 (br s, 4H), 6.37 (br s, 3H), 7.35 (s, 10H), 7.50 (AB, 4H); MS (FAB) m/e 766 (M+H)$^+$.

e) t-butyl N-[2,5-dioxo-3-(S)-[3-[$N^\gamma$-tosyl]-guanidinopropyl]-4-methyl-octahydro -1,4-diazocin-1-yl]-acetate (17)

Compound (16) (1.27 g, 1.66 mmol) and 5% palladium on carbon (200 mg) were suspended in n-butanol and methanol was treated with hydrogen (50 psi) at room temperature for 4 h. The reaction mixture was filtered through Celite® and the solvents were evaporated. The residue was evaporated from toluene and dried under vacuum to yield crude $N^\gamma$-tosyl-$N^\alpha$-methyl-$N^\alpha$-[1-carboxy-3-[[N-[1-carboxylmethyl]-methyl]-amino] propanyl]-arginine.

Approximately 400 mg of the crude $N^\gamma$-tosyl-$N^\alpha$-methyl-$N^\alpha$-[1-carboxy-3-[[N-[1-carboxylmethyl]-methyl]-amino]-propanyl] arginine from above was dissolved in dimethylformamide (200 mL) and cooled to 0° C. Triethylamine (3.0 mL, 21.6 mmol) and diphenylphosphoryl azide (3.10 mL, 14.4 mmol) were added and the solution was warmed slowly to room temperature and stirred for 96 h. The reaction mixture was evaporated under vacuum and the residue was purified by flash chromatography (silica gel, 5% methanol/chloroform) to yield the title compound (17) (116 mg, 30%).

The remaining crude $N^\gamma$-tosyl-$N^\alpha$-methyl-$N^\alpha$-[1-carboxy-3-[[N-[1-carboxylmethyl]-methyl]-amino]-propanyl]-arginine from above (520 mg) was dissolved in dimethylformamide (400 mL) and cooled to 0 ° C. Triethylamine (401 μL, 2.88 mmol) and diphenylphosphoryl azide (414 μL, 1.92 mmol) were added and the resulting solution was warmed slowly to room temperature and stirred for 72 h. The reaction mixture was evaporated under vacuum and the residue was purified by flash chromatography (silica gel, 5% methanol/chloroform) to yield additional (17) (187 mg, 37%). Compound 17: $^1$H NMR (CDCl$_3$) ε 1.42 (s, 9H), 1.50–2.17 (m, 6H), 2.37 (s, 3H), 2.50–3.43 (m, 6H), 2.73 (s, 3H), 3.57–4.73 (m, 2H), 4.75 (t, 1H, J=7.5 Hz), 6.23–6.70 (m, 3H), 7.53 (AB, 4H); MS (FAB) m/e 524 (M+H)$^+$.

f) N-[2,5-dioxo-3-(S)-[3-[$N^\gamma$-tosyl]-guanidinopropyl]-4-methyl-octahydro -1,4-diazocin-1-yl]-acetic acid (18)

Compound (17) (116 mg, 0.222 mmol) was treated with trifluoroacetic acid (4 mL) at room temperature for 4 h. The reaction mixture was evaporated at reduced pressure and the residue evaporated from chloroform/methanol and chloroform/toluene, and dried under vacuum to yield the title compound (18 ) .

g) N-[2,5-dioxo-3-(S)-[3-[$N^\gamma$-tosyl]-guanidinopropyl]-4-methyloctahydro -1,4-diazocin-1-yl]-acetyl γ-benzyl-aspartyl-1-phenyl amide (19)

Compound (18) was dissolved in dimethylformamide and treated with γ-benzyl aspartyl anilide hydrochloride (149 mg, 0.444 mmol), 1-hydroxybenzotriazole (60 mg, 0.444 mmol), 4-methylmorpholine (146 μL, 1.33 mmol) and benzotriazol-1-yloxytris (dimethylamino) phosphonium hexafluorophosphate (196 mg, 0.444 mmol). The resulting solution was stirred at room temperature for 24 h. The reaction mixture was evaporated under vacuum and the residue purified twice by flash chromatography (silica gel, 5% methanol/chloroform) to yield the title compound (19) (121 mg, 73%). Compound (19): $^1$H NMR (CDCl$_3$) ε 1.13–2.13 (m, 6H), 2.13–3.47 (m, 7H), 2.33 (s, 3H), 2.65 (s, 3H), 3.47–5.03 (m, 5H), 5.10 (s, 2H), 6.07–6.70 (m, 3H), 6.93–8.07 (m, 10H), 7.32 (s, 5H), 9.00 (br s, 1H); MS (FAB) m/e 748 (M+H)$^+$.

h) N-[2,5-dioxo-3-(S)-[3-guanidinopropyl]-4-methyl-octahydro-1,4-diazocin-1-yl]-acetyl-aspartyl-1-phenyl amide (20)

Compound (19) (121 mg, 0.162 mmol) was transferred to a Teflon® reaction vessel in methylene chloride, and the solvent was evaporated using a stream of argon. The residue was treated with anhydrous HF (10 mL) at 0° C. for 1 h. After all of the HF was removed under vacuum, the residue was dissolved in 10% aqueous acetic acid and lyophilized. The crude product (52 mg) was purified by reverse phase hplc[5 Apex-ODS; 10×250 mm column; 4.0 mL/min; 82: 18 water-0.1% trifluoroacetic acid:acetonitrile-0.1% trifluoroacetic acid] and lyophilized from 1% aqueous acetic acid to yield the title compound (20). Compound 20: MS (FAB) m/e 504 [M+H]$^+$; HPLC k' 3.00 [5μ Apex-ODS, UV detection at 220 nm, 82: 18 water-0.1% trifluoroacetic acid:acetonitrile-0.1% trifluoroacetic acid], k' 3.56 [5μ Apex-ODS, UV detection at 220 nm, gradient elution, A:water-0.1% trifluoroacetic acid, B: acetonitrile-0.1% trifluoroacetic acid, 5–50% B during 20 min]; TLC Rf 0.11 (silica gel, 4:1:1 butanol:acetic acid:water); TLC Rf 0.42 (silica gel, 1:1:1:1 butanol:acetic acid:water:ethyl acetate).

EXAMPLE 4

Preparation of methyl N-[2.5-dioxo-3-(S)-[3-[$N^\gamma$-tosyl]-guanidinopropyl]-4-methyl-octahydro-1,4-diazocin-1-yl]-acetate (24)

a) methyl N-t-butyloxycarbonyl-N-5-[pent-1-enyl]-glycinate (21)

Methyl N-5-[pent-1-enyl]-glycinate (1) (2.76 g, 17.6 mmol) was dissolved in methylene chloride (75 mL) and treated with di-t-butyl-dicarbonate (4.61 g, 21.2 mmol). The resulting solution was stirred at room temperature for 44 h. The reaction mixture was evaporated at reduced pressure and the residue was purified by flash chromatography (silica gel, 10% ethyl acetate/hexane) to yield the title compound (21) (4.24 g, 94%). Compound 21: $^1$H NMR (CDCl$_3$) ε 1.45 (s, 9H), 1.60 (p, 2H, J=7.5 Hz), 2.07 (q, 2H, J=7.5 Hz), 3.28 (t, 2H, J=7.5 Hz), 3.75 (s, 3H), 3.80–4.10 (m, 2H), 4.88–5.22 (m, 2H), 5.57–6.13 (m, 1H).

b) methyl N-3-[1-carboxybenzyl-propanyl]-glycinate (22)

Compound (21) (4.24 g, 16.5 mmol) was dissolved in a 1:1 mixture of benzene and water (160 mL) and cooled to 0° C. Acetic acid (16 mL), tetra-n-butylammonium bromide (80 mg) and potassium permanganate (8.3 g, 52.5 mmol) were added at 0° C. After 15 min, the ice bath was removed and the reaction stirred at room temperature for 3 h. The reaction mixture was diluted with water and the excess potassium permanganate was quenched by the addition of solid sodium bisulfite. The reaction mixture was acidified with 1N HCl (aqueous) and extracted with ethyl acetate. The combined organic extracts were dried over anhydrous MgSO$_4$, filtered and evaporated at reduced pressure to give crude methyl N-t-butyloxycarbonyl-N-3-[1-carboxybenzyl-propanyl]-glycinate.

The crude methyl N-t-butyloxycarbonyl-N-3-[1-carboxy-benzyl-propanyl]-glycinate from above in methylene chloride was treated with benzyl alcohol (3.41 mL, 33 mmol), N,N-dicyclohexylcarbodiimide (4.09 g, 19.8 mmol) and N,N-dimethylaminopyridine (2.42 g, 19.8 mmol) and the resulting reaction mixture was stirred at room temperature for 72 h. The reaction mixture was filtered; the filtrate was diluted with chloroform, washed with 3N HCl (aqueous), dried over anhydrous MgSO$_4$, filtered and evaporated at reduced pressure to give crude methyl N-t-butyloxycarbonyl-N-3-[1-carboxypropanyl]-glycinate.

Crude methyl N-t-butyloxycarbonyl-N-3-[1-carboxypropanyl]-glycinate was treated with 4N HCl in dioxane at room temperature for 2 h. After evaporation at reduced pressure, the residue was dissolved in ethyl acetate and 5% sodium bicarbonate (aqueous). The organic layer was dried over anhydrous MgSO$_4$, filtered and was evaporated at reduced pressure. The residue was purified using flash chromatography (silica gel, 70% ethyl acetate/hexane) to yield the title compound (22) (2.28 g, 52%). Compound 22: $^1$H NMR (CDCl$_3$) ∈ 1.57 (s, 1H), 1.80 (p, 2H, J=6.8 Hz), 2.43 (t, 2H, J=6.8 Hz), 2.63 (t, 2H, J=6.8 Hz), 3.40 (s, 2H), 3.73 (s, 3H), 5.17 (s, 2H), 7.40 (s, 5H).

c) methyl N-3-[1-carboxybenzyl-propanyl]-N-[N$^\gamma$-tosyl-N$^\alpha$-methyl-N$^\alpha$ -t-butyloxycarbonyl-argininyl]-glycinate (23)

Compound (22) (2.28 g, 8.59 mmol), N$^\gamma$-tosyl-N$^\alpha$-methyl-N$^\alpha$-t-butyloxycarbonyl-arginine (3.8 g, 8.59 mmol), N,N-diisopropylethylamine (5.1 mL, 29.2 mmol), 1-hydroxybenzotriazole (1.39 g, 10.31 mmol) and benzotriazol-1-yloxy-tris (dimethylamino) phosphonium hexafluorophosphate (4.46 g, 10.31 mmol) were dissolved in dimethylformamide and the solution was stirred at room temperature for 90 h. The reaction mixture was evaporated under high vacuum and the residue was purified twice using flash chromatography (silica gel, 60–80% ethyl acetate/hexane; silica gel, 3% methanol/chloroform) to yield the title compound (23) (3.92 g, 66%). Compound 23: $^1$H NMR (CDCl$_3$) ∈ 1.43 (s, 9H), 1.53–3.03 (m, 8H), 2.37 (s, 3H), 2.68 (s, 3H), 3.02–3.60 (m, 4H), 3.72 (s, 3H), 3.87–5.10 (m, 3H), 5.15 (s, 2H), 6.37 (br s, 3H), 7.40 (s, 5H), 7.53 (AB, 4H); MS (FAB) m/e 690 (M+H)$^+$. d) methyl N-[2,5-dioxo-3-(S)-[3-[N$^\gamma$-tosyl]-guanidinopropyl]-4-methyl-octahydro-1,4-diazocin-1-yl]-acetate (24)

Compound (23) (3.92 g, 5.68 mmol) was dissolved in methanol, 5% palladium on carbon (400 mg) suspended in n-butanol was added, and the reaction mixture was hydrogenated at room temperature for 3 h. The reaction mixture was filtered through Celite® and the filtrate was evaporated at reduced pressure to yield crude methyl N-3-[1-carboxypropanyl]-N-[N$^\gamma$-tosyl-N$^\alpha$-methyl-N$^\alpha$-t-butyloxycarbonylargininyl]-glycinate.

The crude methyl N-3-[1-carboxy-propanyl]-N-[N$^\gamma$-tosyl-N$^\alpha$-methyl-N$^\alpha$ -t-butyloxycarbonyl-argininyl]-glycinate was treated with 4N HCl in dioxane at room temperature for 3 h. The reaction mixture was evaporated at reduced pressure and the residue evaporated two times from toluene and dried under vacuum to give crude methyl N-3-[1-carboxy-propanyl]-N-[N$^\gamma$-tosyl-N$^\alpha$-methyl-argininyl]-glycinate hydrochloride.

The crude methyl N-3-[1-carboxy-propanyl]-N-[N$^\gamma$-tosyl-N$^\alpha$-methyl-argininyl]-glycinate hydrochloride was dissolved in dimethylformamide (200 mL) and cooled to 0° C. The solution was then treated with 4-methylmorpholine (375 μL, 3.4 mmol), 1-hydroxybenzotriazole (154 mg, 1.14 mmol) and benzotriazol-1-yloxy-tris(dimethylamino)phosphonium hexafluorophosphate (520 mg, 1.14 mmol). The solution was warmed slowly to room temperature and stirred for 5 d. The reaction mixture was evaporated under vacuum and the residue purified twice by flash chromatography (silica gel, 5–8% methanol/chloroform; silica gel, 7% methanol/chloroform) to yield the title compound (24) (170 mg, 62%). Compound 24: $^1$H NMR (CDCl$_3$) ∈ 1.33–2.10 (m, 6H), 2.33–4.40 (m, 8H), 2.38 (s, 3H), 2.75 (s, 3H), 4.77 (t, 1H, J=7.5 Hz), 6.27–6.77 (m, 3H), 7.53 (q, 4H).

EXAMPLE 5

Preparation of
N-[2,5-dioxo-3-(S)-[3-guanidinopropyl]-4-methyl-octahydro-1,4-diazocin-1-yl]-acetyl-β-alanine (27)

a) benzyl N-t-butyloxycarbonyl-β-alaninate (25)

N-t-Butyloxycarbonyl-β-alanine (2.0 g, 10.6 mmol) in methylene chloride (50 mL) was treated with benzyl alcohol (1.66 mL, 26.0 mmol), N,N-dicyclohexylcarbodiimide (2.39 g, 11.6 mmol) and N,N-dimethylaminopyridine (1.42 g, 11.6 mmol) and the subsequent reaction mixture was stirred at room temperature for 54 h. The reaction mixture was filtered and evaporated at reduced pressure. The residue was purified using flash chromatography (silica gel, 50% ethyl acetate/hexane) to yield the title compound (25) (2.43 g, 82%). $^1$H NMR (CDCl$_3$) ∈ 1.47 (s, 9H), 2.61 (t, 2H, J=6 Hz), 3.45 (q, 2H, J=7.5 Hz), 5.15 (br s, 1H), 5.27 (s, 2H), 7.43 (s, 5H).

b) Synthesis of N-[2,5-dioxo-3-(S)-[3-[N$^\gamma$-tosyl]-guanidinopropyl]-4-methyl-octahydro-1,4-diazocin-1-yl]-acetyl-benzyl-β-alaninate (26)

Compound (25) (517 mg, 1.85 mmol) was treated with 4N HCl in dioxane at room temperature for 2 h. The reaction mixture was evaporated at reduced pressure, evaporated from toluene and then dried under vacuum to give crude benzyl β-alaninate hydrochloride which was used without further purification.

The crude benzyl β-alaninate hydrochloride (183 mg, 0.391 mmol) was dissolved in a mixture of methylene chloride and dimethylformamide (5:1, 12 mL) and the pH of the solution was adjusted to 8 with N,N-diisopropylethylamine (163 μL, 0.934 mmol). Compound (18) prepared above, was added in a mixture of methylene chloride and dimethylformamide (5:1, 12 mL) followed by N,N-dicylcohexylcarbodiimde (136 mg, 0.654 mmol) and N,N-dimethylaminopyridine (80.8 mg, 0.654 mmol). The resulting reaction mixture was stirred at room temperature for 30 h. The reaction mixture was evaporated under vacuum and the residue was purified by flash chromatography (silica gel, 10% methanol/chloroform) to yield the title compound (26) (273 mg, 70%). Compound 26: $^1$H NMR (CDCl$_3$) δ 1.33–2.13 (m, 6H), 2.33 (s, 3H), 2.53 (t, 2H, J=6 Hz), 2.73

(s, 3H), 2.80–4.57 (m, 10H), 4.80 (t, 1H, J=6.8 Hz), 5.16 (s, 2H), 6.28 (br t, 1H), 6.67 (br s, 2H), 6.90 (t, 1H, J=6 Hz), 7.40 (s, 5H), 7.57 (AB, 4H); MS (FAB) m/e 629 (M+H)⁺.

c) N-[2, 5-Dioxo-3-(S)-[3-guanidinopropyl]-4-methyl-octahydro-1,4-diazocin-1-yl]-acetyl-β-alanine (27)

Compound (26) (273 mg, 0.434 mmol) was transfered to a Teflon® reaction vessel in methylene chloride solution. The solvent was evaporated using a stream of argon, and the residue was treated with anhydrous HF (10 mL) at 0° C. for 1 h. After all of the HF was removed under vacuum, the residue was dissolved in 1% aqueous acetic acid and lyophilized. The crude product was purified by gel chromatography (G-15, 1% aqueous acetic acid) to yield the title compound (27). Compound 27:MS (FAB) m/e 385[M+H⁺; HPLC k' 2.08 [5μ Apex-ODS, UV detection at 220 nm, 95:5 water-0.1% trifluoroacetiyc acid:acetonitrile 0.1% trifluoroacetic acid]; TLC $R_f$ 0.16 (silica gel, 4:1:1 butanol:acetic acid:water); TLC $R_f$ 0.38 (silica gel, 1:1:1:1 butanol:acetic acid:water:ethyl acetate).

EXAMPLE 6

Preparation of
N-[2,5-Dioxo-3-(S)-[3-guanidinopropyl]-4-methyl-octahydro
-1,4-diazocin-1-yl]-aspartyl-valinyl acid (30).

a) benzyl N-t-butyloxycarbonyl-γ-benzyl-aspartyl-valinate (28)

N-t-Butyloxycarbonyl-γ-benzyl-aspartic acid (2.0 g, 6.19 mmol) in dimethylformamide (10 mL) was cooled to 0° C. and treated with 1-hydroxybenzotriazole (836 mg, 6.19 mmol) and N,N-dicyclohexylcarbodiimide (1.28 g, 6.19 mmol) and the reaction was stirred for 10 min. In the meantime, benzyl valinate p-toluensulfanate (2.35 g, 6.19 mmol) in dimethylformamide (10 mL) was treated with N,N-diisopropylethylamine (1.08 mL, 6.19 mmol) at room temperature. The free base was then added to the activated acid and the reaction mixture was stirred at 0° C. for 15 min, then at room temperature for 24 h. The reaction mixture was evaporated under vacuum and dissolved in ethyl acetate. This was washed with 5% sodium bicarbonate (aqueous) and 1N HCl, dried over anhydrous MgSO₄, filtered and evaporated at reduced pressure. The residue was purified by flash chromatography (silica gel, 20% ethyl acetate/hexane) to yield the title compound (28) (3.33 g, 100%). Compound 28: ¹H NMR (CDCl₃) ε 0.83 (d, 3H, J=6 Hz), 0.88 (d, 3H, J=6 Hz), 1.45 (s, 9H), 2.50–3.23 (m, 2H), 4.40–4.73 (m, 2H), 5.18 (br s, 4H), 5.78 (d, 1H, J=7.5 Hz), 7.10 (d, 1H, J=9 Hz), 7.38 (s, 10H).

b) benzyl N-[2, 5-dioxo-3-(S)-[3-[Nᵞ-tosyl]-guanidinopropyl]-4-methyl-octahydro -1,4 -diazocin-1-yl]-γ-benzyl-aspartyl-valinate (29)

Compound (28) (1.2 g, 2.34 mmol) was treated with 4N HCl in dioxane at room temperature for 3 h. The reaction mixture was evaporated at reduced pressure, evaporated twice from toluene, once from methanol and the residue was then dried under vacuum to give crude benzyl γ-benzyl-aspartyl-valinate hydrochloride which was used without further purification. Benzyl γ-benzyl-aspartyl-valinate and compound (18) were dissolved in dimethylformamide and treated with 1-hydroxybenzotriazole (199 mg, 1.47 mmol), 4-methylmorpholine (485 μL, 4.41 mmol), and benzotriazol-1-yloxytris (dimethylamino) phosphonium hexafluorophosphate (650 mg, 1.47 mmol) at room temperature and stirred for 96 h. The reaction mixture was evaporated under vacuum and the residue was purified twice using flash chromatography (silica gel, 5% methanol/chloroform; silica gel, 4% methanol/chloroform) to yield the title compound (29) (466 mg, 74%). Compound 29: ¹H NMR (CDCl₃) 5 0.77–1.00 (m, 6H), 1.30–2.02 (m, 6H), 2.35 (s, 3H), 2.62–3.75 (m, 9H), 2.72 (s, 3H), 4.15–5.02 (m, 5H), 5.13 (br s, 4H), 6.25–6.85 (m, 3H), 7.12–8.00 (m, 6H), 7.35 (s, 10H); MS (FAB) m/e 862 (M+H)⁺.

c) N-[2, 5-dioxo-3-(S)-[3-guanidinopropyl]-4-methyl-octahydro-1,4-diazocin-1-yl]-aspartyl-valinyl acid (30)

Compound (29) (367 mg, 0.426 mmol) was transfered to a Teflon® reaction vessel in methylene chloride which was then evaporated using a stream of argon. The residue was treated with anhydrous HF (10 mL) at 0° C. for 1 h. After all of the HF was removed under vacuum, the residue was dissolved in 1% aqueous acetic acid and lyophilized to yield a crude product (193 mg). The crude product was divided into two parts, each of which were purified by gel chromatography (Sephadex G-15, 1% aqueous acetic acid) to yield, after lyophilization, the title compound (30) (144 mg). Compound 30:MS(FAB) m/e 528 [M+H⁺; HPLC k' 2.39 [5μ Apex-ODS, UV detection at 220 nm, 88:12 water-0.1% trifluoroacetic acid:acetonitrile-0.1% trifluoroacetic acid]; HPLC k' 2.02 [5μ Apex-ODS, UV detection at 220 nm, gradient elution, water-(0.1% trifluoroacetic acid B:acetonitrile-0.1% trifluoroacetic acid in acetonitrile) 10–50% B during 20 min]; TLC $R_f$ 0.08 (silica gel, 4:1:1 butanol:acetic acid:water); TLC $R_f$ 0.30 (silica gel, 1:1:1:1 butanol :acetic acid:water:ethyl acetate).

EXAMPLE 7

Preparation of
N-[2,5-Dioxo-3-(S)-[3-guanidinopropyl]-octahydro-
1,4-diazocin-1-yl]-acetyl-aspartyl-1-phenylamide
(35)

a) methyl N-3-[1-carboxybenzyl-propanyl]-N-[Nᵞ-tosyl-Nᵅ-t-butyloxycarbonyl-argininyl]-glycinate (31)

Methyl N-3-[1-carboxybenzyl-propanyl]-glycinate, Compound (22), (2.28 g, 8.59 mmol), Nᵞ-tosyl-Nᵅ-t-butyloxycarbonyl-arginine (Peninsula, 6.13 g, 14.3 mmol), 1-hydroxybenzotriazole (2.12 g, 15.7 mmol) and N,N-dicyclohexylcarbodiimide (2.95 g, 14.3 mmol) were dissolved in dimethylformamide (50 mL) and the solution stirred at room temperature for 24 h. The reaction mixture was filtered, the filtrate was evaporated under vacuum and the residue was purified using flash chromatography (silica gel, 3% methanol/chloroform) to yield the title compound (31) (5.88 g, 61%) Compound 31: ¹H NMR (CDCl₃) δ 1.17–2.55 (m, 8H), 1.38 (s, 9H), 2.35 (s, 3H), 3.00–3.93 (m, 4H), 3.70 (s, 3H), 4.03–4.80 (m, 3H), 5.15 (s, 2H), 5.30–5.63 (m, 1H), 6.50 (br s, 3H), 7.37 (s, 5H), 7.52 (AB, 4H). p b) methyl N-3-[1-carboxy-propanyl]-N-[Nᵞ-tosyl-Nᵅ-t-butyloxycarbonyl-argininyl]-glycinate (32)

Compound (31) (5.88 g, 8.70 mmol) was dissolved in methanol with 5% palladium on carbon (suspended in n-butanol). The reaction mixture was treated with hydrogen at room temperature for 3 h. After sitting overnight under argon, the reaction mixture was filtered through a bed of Celite® and the solvent was evaporated at reduced pressure. The residue was purified using flash chromatography (silica gel, 95:4:1 to 90:8:2 chloroform:methanol:acetic acid) to yield the title compound (32) (3.78 g, 74%). Compound 32: ¹H NMR (CDCl₃) ε 1.38 (s, 9H), 1.50–2.10 (m, 6H), 2.38 (br s, 5H), 2.80–3.63 (m, 4H), 3.70 (s, 3H), 3.83–4.43 (m, 2H), 4.68 (br t, 1H), 5.63 (br d, 1H), 6.42–7.17 (m, 3H), 7.50 (AB, 4H), 9.40 (br s, 1H); MS (FAB) m/e 586 (M+H)$^+$.

c) methyl N-[2,5-dioxo-3-(S)-[3-[N$^\gamma$-tosyl]-guanidinopropyl]-octahydro -1,4-diazocin-1-yl]-acetate (33)

Compound (32) (500 mg, 0.854 mmol), dissolved in methylene chloride, was treated with pentachlorophenol (250 mg, 0.939 mmol) and N,N-dicyclohexylcarbodiimide (176 mg, 0.854 mmol), and the resulting mixture was stirred at room temperature for 24 h. The reaction mixture was filtered and the filtrate evaporated at reduced pressure. The residue was purified using flash chromatography (silica gel, 3% methanol/chloroform) to (635 mg, 89%) the pentachlorophenyl ester of methyl N-3-[1-carboxy-propanyl]-N-[N$^\gamma$-tosyl-N$^\alpha$-t-butyloxycarbonyl -argininyl]-glycinate: $^1$H NMR (CDCl$_3$) ∈ 1.40 (s, 9H), 1.50–2.33 (m, 6H), 2.38 (s, 3H), 2.75 (q, 2H, J=7.5 Hz), 3.07–4.80 (m, 7H), 3.70 (s, 3H), 5.60 (t, 1H, J=7.5 Hz), 6.48 (br s, 3H), 7.53 (AB, 4H).

The pentachlorophenyl ester of methyl N-3-[1-carboxypropanyl ]-N-[N$^\gamma$-tosyl-N$^\alpha$-t-butyloxycarbonyl-argininyl] glycinate was treated with 4N HCl in dioxane at room temperature for 3 h. The reaction mixture was evaporated at reduced pressure and then evaporated from toluene and dried under vacuum. The residue was dissolved in dimethylformamide (60 mL) and the mixture was added dropwise to a solution of N,N-diisopropylethylamine (530 µL, 3.0 mmol) in portions over 18 h, then stirred for 48 h. The solvent was removed under vacuum and the residue was purified using flash chromatography (silica gel, 7% methanol/chloroform) to yield the title compound (33) (294 mg, 83%). Compound 33: $^1$H NMR (CDCl$_3$) ∈ 1.47–2.17 (m, 6H), 2.37 (s, 3H), 2.43–3.57 (m, 5H), 3.70 (s, 3H), 3.80–4.33 (m, 3H), 4.33–4.77 (m, 1H), 6.33–7.00 (m, 4H), 7.53 (AB, 4H); MS (FAB) m/e 468 (M+H)$^+$.

d) N-[2,5-Dioxo-3-(S)-[3-[N$^\gamma$-tosyl]-guanidinopropyl]-octahydro-1,4-diazocin-1-yl]-acetyl γ-benzyl-aspartyl-1-phenyl amide (34 )

Compound (33) (294 mg, 0.628 mmol), dissolved in methanol (2 mL), was treated with 1 mL of 1N NaOH at room temperature for 3 h. The reaction mixture was acidified with 1N HCl and the solvent was evaporated under vacuum. The residue dried under vacuum overnight to give crude N-[2,5-dioxo-3-(S)-[3-[N$^\gamma$-tosyl]-guanidinopropyl]-octahydro-1,4-diazocin-1-yl]-acetic acid.

The crude N-[2,5-dioxo-3-(S)-[3-[N$^\gamma$-tosyl]guanidinopropyl]-octahydro-1,4-diazocin-1-yl]-acetic acid was dissolved in a mixture of methylene chloride and dimethylformamide and was treated with γ-benzyl aspartyl anilide hydrochloride (371 mg, 1.11 mmol), N,N-diisopropylethylamine (193 µL, 1.11 mmol), N,N-dicyclohexylcarbodiimide (130 mg, 0.628 mmol) and N,N-dimethylaminopyridine (77 mg, 0.628 mmol). The resulting reaction mixture was stirred at room temperature for 120 h. The reaction mixture was evaporated under vacuum and the residue was purified using flash chromatography (silica gel, 7% methanol/chloroform) to yield the title compound (34) (313 mg, 68%). Compound 34: $^1$H NMR (CDCl$_3$) ∈ 1.30–2.03 (m, 6H), 2.33 (s, 3H), 2.67–3.47 (m, 6H), 3.57–4.63 (m, 5H), 4.83–5.20 (m, 1H), 5.10 (s, 2H), 6.20–6.80 (m, 4H), 6.96–8.13 (m, 10H), 7.33 (s, 5H), 9.17 (br s, H); MS (FAB) m/e 734 (M+H)$^+$.

e) N-[2,5-dioxo-3-(S)-[3-guanidinopropyl]-octahydro-1, 4-diazocin-1-yl]-acetyl-aspartyl-1-phenyl amide (35).

Compound (34) (277 mg, 0.377 mmol) was transferred to a Teflon® reaction vessel in methylene chloride. The solvent was evaporated using a stream of argon. The residue was treated with anhydrous HF (10 mL) at 0° C. for 1 h. After all of the HF was removed under vacuum, the residue was dissolved in 10% aqueous acetic acid and lyophilized. The crude product was purified by reverse phase hplc [5 µ Apex-ODS, 80:20 water-0.1% trifluoroacetic acid:acetonitrile-0.1% trifluoroacetic acid]. Lyophilization of the product from 1% aqueous acetic acid yields the title compound (35). Compound 35: MS(FAB) m/e 490 [M+H]$^+$; HPLC k' 1.38 [5µ Apex-ODS, UV detection at 220 nm, 80:20 water-0.1% trifluoroacetic acid:acetonitrile-0.1% trifluoroacetic acid]; HPLC k' 4.85 [5µ Apex-ODS, UV detection at 220 nm, gradient elution, A:water-0.1% trifluoroacetic acid, B:acetonitrile-0.1% trifluoroacetic acid, 5–50% B during 20 min] TLC R$_f$ 0.20 (silica gel, 4:1:1 butanol:acetic acid:water); TLC R$_f$ 0.46 (silica gel, 1:1:1:1 butanol:acetic acid:water:ethyl acetate).

EXAMPLE 8

Preparation of Methyl
N-[2,5-dioxo-3-(S)-[3-[N$^\gamma$-tosyl]-guanidinopropyl]-octahydro-1,4-diazocin-1-yl]-acetate (33)—Alternate Method of Cyclization Methyl N-3-[1-carboxy-propanyl]-N-[N$^\gamma$-tosyl-N$^\alpha$-t-butyloxycarbonyl-argininyl]-glycinate (32) (530 mg, 0.905 retool) was treated with 4N HCl in dioxane at room temperature for 2 h. The reaction mixture was evaporated at reduced pressure and the residue was evaporated from toluene and dried under vacuum to give crude methyl N-3-[1-carboxypropanyl]-N-[N$^\gamma$-tosyl-argininyl]-glycinate hydrochloride.

Methyl N-3-[1-carboxy-propanyl]-N-[N$^\gamma$-tosyl-argininyl] glycinate hydrochloride (265 mg, 0.452 mmol) dissolved in dimethylformamide (100 mL), was cooled to 0° C. and treated with N,N-diisopropylethylamine (79 µL, 0.452 mmol), diphenylphosphoryl azide (195 µL, 0.905 mmol) and sodium bicarbonate (190 mg, 2.26 mmol). The reaction was stirred at room temperature for 96 h. The reaction mixture was evaporated under vacuum and the residue was purified using flash chromatography (silica gel, 7% methanol/chloroform) to yield the title compound (33) (78 mg, 37%).

EXAMPLE 9

Preparation of Methyl
N-[3,5-dioxo-3-(S)-[3-[N$^\gamma$-tosyl]-guanidinopropyl]-octahydro-1,4-diazocin-1-yl]-acetate—Alternate Method of Cyclization Methyl N-3-[1-carboxy-propanyl]-N-[N$^\gamma$-tosyl-arginyl] glycinate hydrochloride (265 mg, 0.452 mmol) was treated with 4-methylmorpholine (298 µL, 2.71 mmol), 1-hydroxybenzotriazole (122 mg, 0.905 mmol) and benzotriazol-1-yloxytris (dimethylamino) phosphonium hexafluorophosphate (400 mg, 0.905 mmol) and the solution was stirred at room temperature for 6 d. The reaction mixture was evaporated under vacuum and the residue was purified using flash chromatography (silica gel, 7% methanol/chloroform) to yield the title compound (33) (100 mg, 47%).

EXAMPLE 10

Parenteral Dosage Unit Composition

A preparation which contains 20 mg of the compound of Example 1 as a sterile dry powder is prepared as follows: 80 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

EXAMPLE 11

Oral Dosage Unit Composition

A capsule for oral administration is prepared by mixing and milling 150 mg of the compound of Example 3 with 225 mg of lactose and 15 mg of magnesium stearate. The resulting powder is screened and filled into a hard gelatin capsule.

EXAMPLE 12

Oral Dosage Unit Composition

A tablet for oral administration is prepared by mixing and granulating 40 mg of sucrose, 300 mg of calcium sulfate dihydrate and 100 mg of the compound of Example 3 with a 10% gelatin solution. The wet granules are screened, dried, mixed with 20 mg starch, 10 mg talc and 6 mg stearic acid; and compressed into a tablet.

The above description fully discloses how to make and use this invention. This invention, however, is not limited to the precise embodiments described herein, but encompasses all modifications within the scope of the claims which follow.

What is claimed is:

1. A compound of the formula (I):

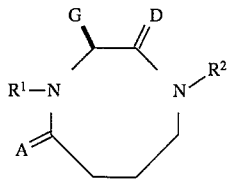

wherein

A and D are independently O or (H,H);

G is $(CHR^7)_t$—Y, $(CHR^7)_p$—$C_{3-7}$cycloalkyl-$(CH_2)_p$—Y or

X is absent, N=CR', C(O) or O;

Y is R'R"N—, R'R"NR'N—, R'R"NR'NCO—, R'$_2$NR'NC(=NR')—, R'ONR'C(=NR')—,

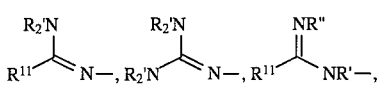

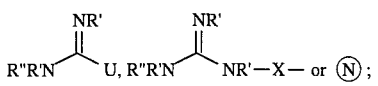

R' is H, $C_{1-6}$alkyl, $C_{3-7}$cycloalkyl-$C_{0-4}$alkyl or Ar—$C_{0-4}$alkyl;

R" is R' or —C(O)R';

$R^1$ is L-M, wherein L is H, $R^6$, $R^6$—J—CO or $R^6$—J—S(O)m, J is O, NH, S or a covalent bond, and M is —NH(CHR$^9$)CO— or a covalent bond:

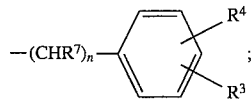

$R^2$ is $(CH_2)_m(C=E)$—Q—$CH(R^3)(R^4)$ or

E is O or (H,H);

Q is a covalent bond, $NR^7$, O, S, $CH_2$ or

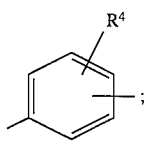

$R^3$ is H, $(CHR^7)_u$—$R^{10}$, or $O(CHR^7)_v$—$R^{10}$ or $(CHR^7)_n CH(NH$—$L)$—$R^{10}$;

$R^4$ is H, $(CHR^7)_u CO$—V, $O(CHR^7)_v CO$—V, $(CHR^7)_u$—W or $O(CHR^7)_v$—W;

U is absent, S or O;

V is W, NHCH($R^5$)CO—W or OCH($R^5$)CO—W;

W is NHR$^6$, OR$^6$ or R$^6$;

$R^5$ and $R^9$ are H $C_{1-6}$alkyl, $C_{3-6}$cycloalkyl, $(CH_2)_n$—Ar, or $(CH_2)_q Z$, where Z is $C_{3-6}$cycloalkyl OH, NH$_2$, SH, S—$C_{1-4}$alkyl, CO$_2$R$^8$, CONH$_2$ or NHC(=NH)NH$_2$;

$R^6$ is H, $(CHR^7)_r$—H, $(CHR^7)_r$—$C_{3-6}$cycloalkyl, $(CHR^7)_r$—Ar;

$R^7$ is H or $C_{1-4}$alkyl;

$R^8$ is H or C 1–4alkyl;

$R^{10}$ is CO$_2$H, SO$_3$H or 5-tetrazolyl;

$R^{11}$ is R', —CF$_3$, —SR', or —OR';

Ar is phenyl or naphthyl, or phenyl or naphthyl substituted by one or two $C_{1-4}$alkyl, $C_{1-4}$alkoxy, $C_{1-5}$alkylthio, CO$_2$R', CON(R')$_2$, NR'$_2$,hydroxy, halogen, trifluoromethyl or nitro groups;

m is 1 or 2;

n is 0 to 9;

p is 0 to 2;

q is 1 to 4;

r is 0 to 4;

t is 2 to 5;

u is 0 to 4;

v is 1 to 3;

or a pharmaceutically acceptable salt thereof.

2. A compound according to claim 1 wherein D and E are O.

3. A compound according to claim 1 wherein $R^1$ is methyl, acetyl or benzoyl.

4. A compound according to claim 1 wherein $R^2$ is CH$_2$CONHCH (R$^3$)CO—V.

5. A compound according to claim 4 wherein V is NHPh.

6. A compound according to claim 5 wherein G is $(CH_2)_3$NHC(=NH)NH$_2$.

7. A compound of the formula (VI):

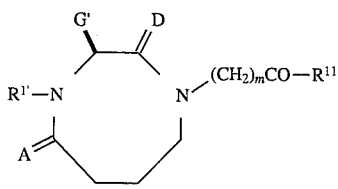

wherein
R¹' is R¹,
G' is G,
$R^{11}$ is $C_{1-6}$alkyl or $(CH_2)Ar$; and
A, D, G, R¹, Ar and m are as defined in claim 1.

8. A compound according to claim 1 which is:

N-[2-oxo-3-(S)-[3-guanidinopropyl]-octahydro-1,4-diazocin-1-yl]-acetyl-aspartyl-1-phenylamide;

N-[2-oxo-3-(S)-[3-guanidinopropyl]-4-acetyl-octahydro-1,4-diazocin-1-yl]-acetyl-aspartyl-1-phenylamide;

N-[2,5-dioxo-3-(S)-[3-guanidinopropyl]-4-methyl-octahydro-1,4-diazocin-1-yl]-acetyl-aspartyl-1-phenylamide;

N-[2,5-dioxo-3-(S)-[3-guanidinopropyl]-4-methyl-octahydro-1,4-diazocin-1-yl]-acetyl-β-alanine;

N-[2,5-dioxo-3-(S)-[3-guanidinopropyl]-4-methyl-octahydro-1,4-diazocin-1-yl]-aspartyl-valinyl acid; or N-[2,5-dioxo-3-(S)-[3-guanidinopropyl]-octahydro-1,4-diazocin-1-yl]-acetyl-aspartyl-1-phenylamide.

9. A pharmaceutical composition which comprises an effective amount of a compound according to claim 1 and a pharmaceutically acceptable carrier.

10. A method for effecting inhibition of platelet aggregation which comprises administering to a mammal in need thereof, an effective amount of a compound according to claim 1.

* * * * *